(12) United States Patent
Freeman et al.

(10) Patent No.: US 11,097,118 B2
(45) Date of Patent: Aug. 24, 2021

(54) MULTI-PATH TRANSTHORACIC DEFIBRILLATION AND CARDIOVERSION

(71) Applicant: ZOLL Medical Corporation, Chelmsford, MA (US)

(72) Inventors: Gary A Freeman, Waltham, MA (US); James E Brewer, Lino Lakes, MN (US); Michael L Lopin, Newton, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 445 days.

(21) Appl. No.: 15/879,532

(22) Filed: Jan. 25, 2018

(65) Prior Publication Data
US 2018/0243575 A1 Aug. 30, 2018

Related U.S. Application Data

(60) Continuation of application No. 14/930,576, filed on Nov. 2, 2015, now Pat. No. 10,022,550, which is a
(Continued)

(51) Int. Cl.
*A61N 1/39* (2006.01)
*A61N 1/04* (2006.01)
*A61B 5/0536* (2021.01)

(52) U.S. Cl.
CPC .......... *A61N 1/3912* (2013.01); *A61N 1/046* (2013.01); *A61N 1/3918* (2013.01);
(Continued)

(58) Field of Classification Search
CPC .............................. A61N 1/046; A61N 1/3918
See application file for complete search history.

(56) References Cited

U.S. PATENT DOCUMENTS 2,590,876 A   4/1952   Landauer
2,622,601 A   12/1952  Nemec
(Continued)

FOREIGN PATENT DOCUMENTS

EP   0057048   8/1982
EP   0518546   12/1992
(Continued)

OTHER PUBLICATIONS

Entcheva, "Patterns of and Mechanisms for Shock-Induced Polarization in the Heart: A Bidomain Analysis," IEEE Trans. Biomed. Eng., 46:260-270 (1999).
(Continued)

*Primary Examiner* — Alyssa M Alter
(74) *Attorney, Agent, or Firm* — ZOLL Medical Corporation

(57) ABSTRACT

A defibrillation system for synchronized cardioversion of a patient includes a first housing that includes a measurement circuit configured to receive electrocardiogram (ECG) signals and measure ECG parameters based on the ECG signals, and a first processor configured to analyze the ECG parameters, and initiate communication of a synchronization signal for a second processor for delivery of one or more defibrillation pulses and further includes a second housing that is separate from and external to the first housing and that includes a shock delivery circuit, and the second processor which is configured to receive the communication of the synchronization signal from the first processor, and control the shock delivery circuit to deliver the one or more defibrillation pulses in response to the synchronization signal.

18 Claims, 25 Drawing Sheets

Related U.S. Application Data division of application No. 10/960,311, filed on Oct. 6, 2004, now Pat. No. 9,174,061, which is a continuation-in-part of application No. 10/712,308, filed on Nov. 13, 2003, now abandoned.

(52) U.S. Cl.
CPC .......... *A61N 1/3987* (2013.01); *A61B 5/0536* (2013.01); *A61N 1/3906* (2013.01); *A61N 1/3937* (2013.01)

(56) References Cited

U.S. PATENT DOCUMENTS

| | | |
|---|---|---|
| 3,077,884 A | 2/1963 | Batrow et al. |
| 3,543,761 A | 12/1970 | Bradley |
| 3,605,754 A | 9/1971 | Jaros et al. |
| 3,626,926 A | 12/1971 | Kuzin et al. |
| 3,774,620 A | 11/1973 | Hansjurgens |
| 3,825,015 A | 7/1974 | Berkovits |
| 3,860,009 A | 1/1975 | Bell et al. |
| 3,888,261 A | 6/1975 | Maurer |
| 3,895,639 A | 7/1975 | Rodler |
| 3,942,536 A | 3/1976 | Mirowski et al. |
| 3,958,577 A | 5/1976 | Rodler |
| 4,023,574 A | 5/1977 | Nemec |
| 4,148,321 A | 4/1979 | Wyss et al. |
| 4,177,817 A | 12/1979 | Bevilacqua |
| 4,280,504 A | 7/1981 | Rodler |
| 4,291,699 A | 9/1981 | Geddes et al. |
| 4,331,157 A | 5/1982 | Keller, Jr. et al. |
| 4,355,646 A | 10/1982 | Kallok et al. |
| 4,372,319 A | 2/1983 | Ichinomiya et al. |
| 4,401,121 A | 8/1983 | Rodler |
| 4,444,195 A | 4/1984 | Gold |
| 4,448,199 A | 5/1984 | Schmid |
| 4,467,807 A | 8/1984 | Bornzin |
| 4,548,203 A | 10/1985 | Tacker, Jr. et al. |
| 4,576,170 A | 3/1986 | Bradley et al. |
| 4,595,010 A | 6/1986 | Radke |
| 4,637,397 A | 1/1987 | Jones et al. |
| 4,641,656 A | 2/1987 | Smits |
| 4,708,145 A | 11/1987 | Tacker, Jr. et al. |
| 4,727,877 A | 3/1988 | Kallok |
| 4,768,512 A | 9/1988 | Imran |
| 4,787,389 A | 11/1988 | Tarj An |
| 4,800,883 A | 1/1989 | Winstrom |
| 4,821,723 A | 4/1989 | Baker, Jr. et al. |
| 4,823,796 A | 4/1989 | Benson |
| 4,830,006 A | 5/1989 | Hulaska et al. |
| 4,928,690 A | 5/1990 | Heilman et al. |
| 4,932,407 A | 6/1990 | Williams |
| 4,953,551 A | 9/1990 | Mehra et al. |
| 5,107,834 A | 4/1992 | Ideker et al. |
| 5,111,812 A | 5/1992 | Swanson et al. |
| 5,163,427 A | 11/1992 | Keimel |
| 5,184,620 A | 2/1993 | Cudahy et al. |
| 5,205,284 A | 4/1993 | Freeman |
| 5,209,229 A | 5/1993 | Gilli |
| 5,224,475 A | 7/1993 | Berg et al. |
| 5,230,336 A | 7/1993 | Fain et al. |
| 5,281,219 A | 1/1994 | Kallok |
| 5,306,291 A | 4/1994 | Kroll et al. |
| 5,314,459 A | 5/1994 | Swanson et al. |
| 5,324,309 A | 6/1994 | Kallok |
| 5,330,506 A | 7/1994 | Alferness et al. |
| 5,344,429 A | 9/1994 | Smits |
| 5,344,430 A | 9/1994 | Berg et al. |
| 5,360,435 A | 11/1994 | DeGroot |
| 5,391,187 A | 2/1995 | Freeman |
| 5,411,525 A | 5/1995 | Swanson et al. |
| 5,423,873 A | 6/1995 | Neubauer et al. |
| 5,431,688 A | 7/1995 | Freeman |
| 5,441,518 A | 8/1995 | Adams et al. |
| 5,447,519 A | 9/1995 | Peterson |
| 5,466,256 A | 11/1995 | McAdams et al. |
| 5,620,470 A | 4/1997 | Gliner et al. |
| 5,678,545 A | 10/1997 | Stratbucker |
| 5,725,560 A | 3/1998 | Brink |
| 5,728,139 A | 3/1998 | Post |
| 5,735,878 A | 4/1998 | Kroll et al. |
| 5,766,226 A | 6/1998 | Pedersen |
| 5,800,465 A | 9/1998 | Thompson et al. |
| 5,855,592 A | 1/1999 | McGee et al. |
| 5,865,838 A | 2/1999 | Obel et al. |
| 5,891,172 A | 4/1999 | Stendahl |
| 5,904,706 A | 5/1999 | Ayati et al. |
| 5,916,243 A | 6/1999 | KenKnight et al. |
| 5,928,270 A | 7/1999 | Ramsey, III |
| 6,096,063 A | 8/2000 | Lopin et al. |
| 6,134,479 A | 10/2000 | Brewer et al. |
| 6,148,233 A | 11/2000 | Owen et al. |
| 6,148,234 A | 11/2000 | Struble |
| 6,178,351 B1 | 1/2001 | Mower |
| 6,213,960 B1 | 4/2001 | Sherman et al. |
| 6,253,106 B1 | 6/2001 | Legay et al. |
| 6,337,995 B1 | 1/2002 | Mower |
| 6,341,234 B1 | 1/2002 | Thong et al. |
| 6,405,084 B2 | 6/2002 | Plicchi et al. |
| 6,411,845 B1 | 6/2002 | Mower |
| 6,473,645 B1 | 10/2002 | Levine |
| 6,484,057 B2 | 11/2002 | Ideker et al. |
| 6,516,231 B1 | 2/2003 | Flammang |
| 6,549,806 B1 | 4/2003 | Kroll |
| 6,606,516 B2 | 8/2003 | Levine |
| 2003/0055459 A1 | 3/2003 | Lyster et al. |
| 2003/0163166 A1 | 8/2003 | Sweeney et al. |
| 2012/0158075 A1* | 6/2012 | Kaib .................. A61N 1/0476 607/7 |

FOREIGN PATENT DOCUMENTS

| | | |
|---|---|---|
| EP | 0602356 A3 | 12/1995 |
| EP | 1118353 | 7/2001 |
| FR | 2257312 | 8/1975 |
| JP | 62-275471 | 11/1987 |
| JP | 2001-046520 | 2/2001 |
| JP | 2001-170019 | 6/2001 |
| WO | 91/19535 | 12/1991 |
| WO | 93/01861 | 2/1993 |
| WO | 95/24155 | 9/1995 |
| WO | 98/47563 | 10/1998 |
| WO | 02/24062 | 3/2002 |

OTHER PUBLICATIONS

Alferness et al., "Multiple External Pacing Electrode Summation in Dogs," Journal of Am. College of Cardiology, Feb. 1991, vol. 17, No. 2 (Supplement A).

Hua et al., "Effect of the Measurement Method on Noise Handling and Image Quality of EIT Imaging"; Proc. Annu. Int. Conf. IEEE Engineering in Medicine and Biology Society; 9:1429-1430; 1987.

Efimov, Am, J. Physiol. Heart Circ. Physiol.; 279:H1055-70; 2000.

Geddes et al., "Electroventilation," American Journal of Emergency Medicine, vol. 3, No. 4, pp. 338-339 (Jul. 1985).

Geddes, "A Short History of the Electrical Stimulation of Excitable Tissue Including Electrotherapeutic Applications," Supp. to the Physiologist, vol. 27, No. 1 (Feb. 1984).

Geddes, L.A. et al., "Fundamental Criteria Underlying the Efficacy and Safety of Defibrillating Current Waveforms"; Med. & Biol. Eng. & Comp.; vol. 23; pp. 122-130; 1985.

Geddes, L.A. et al., "The Prediction of the Impedance of the Thorax to Defibrillating Current"; Medical Instrumentation; vol. 10, No. 3; May-Jun. 1976.

Jones, Douglas L. et al.; "Internal Cardiac Defibrillation in Man: Pronounced Improvement with Sequential Pulse Delivery to Two Different Lead Orientations"; Circulation; vol. 73, No. 3; pp. 484-491; Mar. 1986.

Jones, Janice L. et al.; "Decreased Arrhythmias in Cultured Myocardial Cells Following High Intensity Electric Field Stimulation with Biphasic Rectangular Waveforms"; Federation Proceedings Abs.; vol . 42, n. 4; 1983.

(56) References Cited

OTHER PUBLICATIONS

Jones, Janice L. et al., "Decreased Defibrillator-Induced Dysfunction with Biphasic Rectangular Waveforms"; American Journal of Physiology; vol. 247; No. 5; 1984.
Schuder et al., " Development of Automatic Implanted Defibrillator"; University of Missouri; Grant No. 5-ROL-HE-21674-04; Devices & Tech, Branch Contractors Meeting Proc.; p. 206; 1981.
Jones, Janice L. et al; "Improved Defibrillator Waveform Safety Factor with Biphasic Waveforms"; The American Physiological Society; pp. H60-H65; 1983.
Jones, J.L. et al.; "Reduced Excitation Threshold in Potassium Depolarized Myocardial Cells with Symmetrical Biphasic Waveforms"; J. of Mol. & Cell. Cardiol.; vol. 17, No. 12; abst. No. 39; p. 27; 1985.
Kahn et al., "Technical Aspects of Electrical Stimulation Devices," Med. Progr. Technol., vol. 1, No. 2, pp. 58-68 (1972).
Kerber, Richard E. et al.; "Advance Prediction of Transthoracic Impedance in Human Defibrillation and Cardioversion: Importance of Impedance in Determining the Success of Low-Energy Shocks"; Circulation; vol. 70, No. 2; pp. 303-308; Aug. 1984.
Kerber, Richard E. et al.; "Energy, Current, and Success in Defibrillation and Cardioversion: Clinical Studies Using an Automated Impedance-Based Method of Energy Adjustment"; Circulation; vol. 77, No. 5; May 1988.
Schuder, J.C. et al.; "Asymmetrical Bidirectional Wave Defibrillation in Calves"; Proc. of the 35th Annual Conf. oon Eng. in Medicine and Biology; vol, 24; p. 41; 1982.
Schuder, John C. et al.; "Defibrillation of 100kg Calves with Asymmetrical Bidirectional, Rectangular Pulses"; Cardiovascular Research; vol. 18; pp. 419-426; 1984.
Schuder, John C, et al; "Optimal Biphasic Waveform Morphology for Canine Defibrillation with a Transvenous Catheter and Subcutaneous Patch System"; Circulation Supplement; Abstracts of the $61^{st}$ Scientific Session; Part II, vol. 78; No. 4; p. II-219; 1988.
Jones et al.; "Defibrillator Waveshape Optimization"; Case Western University; Grant No. 5-R01- HL24606-03; Devices and Tech. Branch Contractors Meeting Program; p. 135; 1982.
Schuder, John C. et al.; "Experimental Ventricular Defibrillation with an Automatic and Completely Implanted Systems"; Trans. Amer. SOC. Artif. Int. Organs; vol. 16; pp. 207-212; 1970.
Schuder, John C. et al.; "Transthoracic Ventricular Defibrillation in the 100 kg Calf with Symmetrical One-Cycle Bidirectional Rectangular Wave Stimuli"; IEEE Trans. on Biomedical Eng.; vol. BME-30, No. 7; Jul. 1983.
Schuder, John C. et al.; "Transthoracic Ventricular Defibrillation in the 100 kg Calf with Untruncated and Truncated Exponential Stimuli"; IEEE Trans. on Biomedical Eng.; vol, BME-27, No, 1; Jan. 1980.

Schuder, J.C. et al.; "Ultrahigh-Energy Hydrogen Thyratron/SCR Bidirectional Waveform Defibrillator"; Medical & Biological Engineering & Computing; vol. 20; pp. 419-424; 1982.
Schechter, "Background of Clinical Electrostimulation; VII. Modern era of artificial cardiac pace makers," New York State Journal of Medicine, pp. 1166-1190 (May 15, 1972).
Tang, Anthony S.L. et al.; "Strength Duration Curve for Ventricular Defibrillation Using Biphasic Waveforms"; PACE, vol. 10; No. 2; p. 418; 1987.
Tang, Anthony S.L. et al.; "Ventricular Defibrillation Using Biphasic Waveforms of Different Phasic Duration"; PACE; vol. 10, No. 2; p. 417; 1987.
Tang, Anthony S.L. et al.; "Ventricular Defibrillation Using Biphasic Waveforms; The Importance of Phasic Duration"; JACC; vol. 13, No. 1; pp. 207-214; 1989.
Lown, B. et al.; "Sounding Boards the Energy for Ventricular Defibrillation—Too Little or Too Much?"; NEJMAG 298(22) 1213-1264 (1978).
Tacker, W.A. et al.; "Energy Dosage for Human Transchest Electrical Ventricular Defibrillation"; NEJMAG 290(4) 175-234 (1974).
Warner, E.D. et al.; "Myocardial Injury From Transthoracic Defibrillator Countershock"; Arch. . Pathol., vol. 99; pp. 55-59; 1975.
Jones, J.L. et al.; "Response of Cultured Myocardial Cells to Countershock-Type Electric Field Stimulation"; Am. J. Physiol., vol. 235; pp. H214-H222; 1978.
Patton, J.N. et al., "Current Required for Ventricular Defibrillation"; Br. Med, J., vol. 1, pp. 513-514; 1979.
Kerber, R.E. et al.; "Automated Impedance-Based Energy Adjustment for Defibrillation: Experimental Studies"; Circ., vol. 71; No. 1; pp. 136-140; 1985.
Bo, W.J. et al.; Basic Atlas of Cross-Sectional Anatomy; Table of Contents; Phil., PA., Saunders, 1980.
Fujimoto, L.K. et al., "Human Thoracic Anatomy Based on Computed Tomography for Development of a Totally Implantable Left Ventricular Assist System"; Artificial Organs 8(4):436-444 (1984).
Jacobs, G.B. et al.; "Human Thoracic Anatomy Relevant to Implantable Artificial Hearts," Artificial Organs; vol. 2; No. 1; pp. 64-82; 1978.
Lee, M.M.C. et al.; "Postmortem Studies of Skinfold Caliper Measurement and Actual Thickness of Skin and Subcutaneous Tissue"; Human Biol., 37:91-103;1965.
Oberman, A. et al.; "Heart Size of Adults in a Natural Population—Tecumseh, Michigan"; Circulation, 35:724-733,1967.
Schnittger, I. et al.; "Standardized Intracardiac Measurements of Two-Dimensional Echocardiography"; JACC 2(5):934-38; 1983.
Geddes, L.A. et al.; "The Specific Resistance of Biological Material—A Compendium of Data for the Biomedical Engineer and Physiologist," Med. & Bio. Eng.; vol. 5; pp. 271-293, 1967.
Kerber et al., "Overlapping Sequential Pulses—A New Waveform for Transthorac Defibrillation," Circulation, vol. 89, No. 5, pp. 2396-2379 (May 1994).

* cited by examiner

{6,3}

{4,4}

{3,6}

$V_m$ at the end of shock

Arrhythmogenesis

92

Arrhythmogenesis

Inspiration

Expiration

MULTI-PATH TRANSTHORACIC DEFIBRILLATION AND CARDIOVERSION

CROSS-REFERENCE TO RELATED APPLICATIONS

This application is a continuation application under 35 USC § 120 to U.S. patent application Ser. No. 14/930,576, filed on Nov. 2, 2015 which is a divisional application of U.S. patent application Ser. No. 10/960,311, filed on Oct. 6, 2004 and issued as U.S. Pat. No. 9,174,061 which is a continuation-in-part application of and claims priority to U.S. application Ser. No. 10/712,308, filed on Nov. 13, 2003 and expressly abandoned. All subject matter set forth in the above referenced applications is hereby incorporated by reference in its entirety into the present application as if fully set forth herein.

TECHNICAL FIELD

This invention relates to transthoracic defibrillation and cardioversion (i.e., defibrillation or cardioversion performed using electrodes external to the thoracic cavity).

BACKGROUND

Normally, electrochemical activity within a human heart causes the organ's muscle fibers to contract and relax in a synchronized manner. This synchronized action of the heart's musculature results in the effective pumping of blood from the ventricles to the body's vital organs. In the case of ventricular fibrillation (VF), however, abnormal electrical activity within the heart causes the individual muscle fibers to contract in an unsynchronized and chaotic way. As a result of this loss of synchronization, the heart loses its ability to effectively pump blood. Defibrillators produce a large current pulse that disrupts the chaotic electrical activity of the heart associated with ventricular fibrillation and provides the heart's electrochemical system with the opportunity to re-synchronize itself. Once organized electrical activity is restored, synchronized muscle contractions usually follow, leading to the restoration of effective cardiac pumping.

First described in humans in 1956, transthoracic defibrillation has become the primary therapy for cardiac arrest, ventricular tachycardia (VT), and atrial fibrillation (AF). Monophasic waveforms dominated until 1996, when the first biphasic waveform became available for clinical use. Attempts have also been made to use multiple electrode systems to improve defibrillation efficacy. While biphasic waveforms and multiple-electrode systems have shown improved efficacy relative to monophasic defibrillation, there is still significant room for improvement: shock success rate for ventricular fibrillation (VF) remains less than 70% even with the most recent biphasic technology.

Cardiac fibrillation and defibrillation are still poorly understood and several hypotheses have been promulgated to explain the mechanisms of defibrillation. The concept termed the critical mass hypothesis posits that a defibrillation shock is successful because it extinguishes activation fronts within a critical mass of muscle by depolarizing all non-refractory tissue within a critical mass. The upper limit of vulnerability (ULV) theory hypothesizes that a shock will be successful when, in addition to terminating ventricular fibrillation (VF) wavefronts by prolonging refractoriness in the myocardium ahead of the wavefront, the shock also must not initiate new fibrillation-causing wavefronts at the border of the shock-depolarized region. A shock may be of sufficient intensity to depolarize the myocardium but not be of high enough intensity to prevent new activation fronts, thus resulting in a failed defibrillation attempt. The critical point hypothesis, related to the ULV theory, states that a shock must not create a critical point where a critical voltage gradient intersects with a critical point of refractoriness. These critical points are the initiation points of refibrillation. The "extension of refractoriness" theory states that the shock-induced depolarization of the fibrillating cardiac tissue extends the period of refractoriness to incoming VF wavefronts and as a result terminates VF. Other theories, related to the ULV hypothesis are "progressive depolarization" and "propagated graded (progressive) response cellular depolarization hypothesis".

The theory of Virtual Electrode Polarization (VEP) describes the phenomena by which, because of current flow within a partially conductive medium (the myocardium) contained within another partially conductive medium (blood of the cardiac chambers, lungs, interstitial fluids and other organs within the thoracic cavity), myocardial polarization during defibrillation is characterized by the simultaneous presence of positive and negative areas of polarization adjacent to each other. "Phase Singularity" as defined within the context of VEP is a critical point that is surrounded by positively polarized (equivalent to "depolarized" in the conventional electrophysiology nomenclature), non-polarized and negatively polarized (equivalent to "hyperpolarized") areas. These phase singularities are the source of re-initiation of fibrillation. Post shock excitations initiate in the non-polarized regions between the positively and negatively polarized areas through a process termed "break excitation." The break excitations propagate through the shock-induced non-polarized regions termed "excitable gaps", and if the positively polarized regions have recovered excitability, then a re-entrant circuit at which fibrillation may initiate is formed. The upper limit of vulnerability (ULV) is attained when the areal extent of the excitable gaps is sufficiently minimized, or the shock induced voltage gradient is sufficient to cause rapid propagation of the excitation in the excitable gap, or the extension of refractoriness is sufficient to prevent further advance of the break excitations into the depolarized tissue. With biphasic defibrillation, the second phase of the shock tends to nullify the VEP effect by depolarizing the negatively polarized tissue. Since less energy is needed to depolarize repolarized tissue than further depolarize already depolarized tissue, effective biphasic defibrillation achieves nearly complete depolarization of the myocardium by reversing the negative polarization while maintaining the positive polarization. There remain, however, excitable gaps with biphasic waveforms, albeit reduced in scope relative to monophasic waveforms.

Theoretical approaches to stimulation employing current summation of multiple current sources have been used in the past to produce in the overlap region an additive current or integrated myocardial response sufficient to cause stimulation or defibrillation while the singular current vectors would not. The approach does not address the issue that insufficiently stimulated tissue may remain in the excitable gap that may result in refibrillation.

The concept of current equalization has been promulgated as a means of understanding stimulation. The general approach is to equalize the current distribution across the heart and concentrate the current in the muscular areas of the heart. This approach does not address the generation of the excitable gap, which will still be present. As understood within the context of the VEP effect, uniform current distributions still result in an excitable gap. In fact, a uniform current distribution is not an especially relevant concept within the context of a physiological system such as that of the human thorax where conductances of the organs, muscle, fluids and bone may vary by a factor of 100. Within such a system, current distributions will not be uniform. Even in a simplified, two-conductance system, an applied uniform field will result in a non-uniform current distribution due to the difference in conductances.

The technique of superposed, multiple vector physiologic tissue stimulation has been employed as early as 1948 by Nemec, as disclosed in U.S. Pat. No. 2,622,601, in which a nerve or muscle stimulator is described employing two stimulation waveform generators with multiple sets of electrode. Each waveform is an alternating current electrical signal with the difference between the two frequencies set to 1-100 Hz. In the areas of tissue that are exposed to currents from both sources—the regions of current superposition—a beat frequency equal to the frequency difference will be generated that is capable of stimulating the physiological tissue. U.S. Pat. No. 3,774,620 added the concept of superposition of two or more AC currents that by themselves have no stimulative effect, the currents differing from each other by a low value, with an optimum interference in the treatment area. Similar methods were employed in U.S. Pat. Nos. 3,774,620, 3,895,639, 4,023,574, and 4,440,121. In these and much of the subsequent art, the regions of interest were those areas where the current from the multiple sources overlapped. The summation current in the overlap region would result in a beat frequency or additive current, which would be sufficient to cause stimulation while the singular current vectors would not.

The earliest cardioverters and defibrillators generated either a single burst of alternating current or a single pulse for application to the heart to cause cardioversion or defibrillation. However, the use of multiple pulses to accomplish cardioversion or defibrillation has also been in extensively researched. U.S. Pat. No. 3,605,754 discloses an early double pulse heart defibrillator employing two capacitors that are successively discharged between a single pair of electrodes. Multiple-electrode systems have been employed for implantable pacemakers and defibrillators. For example, sequential pulse multiple electrode systems are disclosed in U.S. Pat. Nos. 4,291,699, 4,641,656, 4,708,145, 4,727,877 4,932,407, and 5,107,834. Sequential-pulse systems operate based on the assumption that sequential defibrillation pulses, delivered between differing electrode pairs have an integrative effect, due to the non-linear action potential response of cardiac tissue, such that the overall energy requirements to achieve defibrillation are less than the energy levels required to accomplish defibrillation using a single pair of electrodes. An alternative approach to multiple-electrode, sequential-pulse defibrillation is disclosed in U.S. Pat. No. 4,641,656. One electrode pair may include a right ventricular electrode and a coronary sinus electrode, and the second electrode pair may include a right ventricular electrode and a subcutaneous patch electrode, with the right ventricular electrode serving as a common electrode to both electrode pairs. An alternative multiple-electrode, simultaneous-pulse system is disclosed in U.S. Pat. No. 4,953,551, employing right ventricular, superior vena cava and subcutaneous patch electrodes. U.S. Pat. No. 4,953,551 discloses simultaneous delivery of pulses between the superior vena cava and the right ventricle and between the right ventricle and a subcutaneous electrode. In U.S. Pat. No. 5,163,427, two capacitor banks are provided which are simultaneously charged and then successfully or simultaneously discharged between different pairs of electrodes.

French Patent No. 2,257,312 discloses sequential pulse defibrillators employing multiple electrodes arranged in and around the heart. In that disclosure, alternating current (AC) defibrillation pulses are sequentially delivered such that each successively activated electrode pair defines a pulse vector, and such that the pulse vectors scan in a rotational fashion through the heart tissue. Pulses are delivered immediately following one another, or may overlap one another for some unspecified period. U.S. Pat. No. 5,324,309 describes overlapping dual pathway pulses where there is an intermediate current vector during the overlap period. U.S. Pat. No. 5,766,226 describes a similar configuration in which the intermediate current vector changes direction and is made to cycle back and forth during the shock pulse. A similar configuration is described in U.S. Pat. No. 5,800,465. U.S. Pat. No. 5,330,506 describes a multi-pathway pacing method where each individual path is a subthreshold stimulus while the current level in the region of superposition is suprathreshold. The current vector in the region of superposition can be steered by varying the timing of the individual pulse onsets. U.S. Pat. No. 5,431,688 describes a multi-electrode, focused waveform, with interposed pulse trains. These techniques have similar deficits in that, while they are able to reduce the excitable gap to some extent via the rotating vector produced by the overlapping of the currents, regions of excitable gap will remain that can still trigger refibrillation.

U.S. Pat. No. 6,148,233 describes a multi-contact electrode composed of multiple small active areas, each active area of a size too small to defibrillate. Each active area is connected to the same current source. Division of the electrode into plural active areas is intended to provide a means of reducing skin sensitization from long-term wear of the electrodes.

SUMMARY

In a first aspect, the invention features a transthoracic defibrillator for external defibrillation, the defibrillator comprising three or more electrodes configured to be attached to the thorax of a patient to establish at least two electrical paths across the thoracic cavity and through the heart of the patient, cables to connect the three or more electrodes to a defibrillator circuit contained in a defibrillator housing, wherein the defibrillator circuit has the capability to deliver a different defibrillation waveform across each of the at least two electrical paths.

Preferred implementations of this aspect of the invention may incorporate one or more of the following. The different defibrillation waveforms may differ in at least one waveform parameter. The defibrillator circuit may have the capability to deliver the same defibrillation waveform across each of the at least two electrical, paths. The defibrillator circuit may include a processing unit for determining an transthoracic impedance distribution and for selecting the waveform parameter of the at least two electrical paths based on the transthoracic impedance distribution. The transthoracic impedance distribution may be two dimensional. The transthoracic impedance distribution may be determined by measuring impedances between locations on the thorax. Measuring impedances between locations on the thorax may comprise measuring impedances between the electrodes. The transthoracic impedance distribution may be measured using electrical impedance tomography (EIT). The transthoracic impedance distribution may be measured using an imaging technique to determine positions of tissue regions, and computing the transthoracic impedance distribution from the positions of tissue regions and resistivities of the tissues. The imaging technique may comprise ultrasound imaging. The imaging technique may employ at least one transducer element integrated into a defibrillation pad supporting at least one of the electrodes. At least one parameter of each waveform may be one of tilt, duration, current, or voltage. The waveforms may be biphasic. The waveforms may be monophasic. The waveforms may be multiphasic. The waveforms may be interlaced. At least one parameter of each waveform may be one of tilt, duration, current, voltage, first phase duration, second phase duration, first phase average current. The waveforms across different electrical paths may be overlapping in time by at least 1 millisecond but by less than 80 percent of the duration of the shortest of the waveforms. The waveforms across different electrical paths may be delivered simultaneously. The waveforms across different electrical paths may be delivered sequentially without overlapping in time. At least one waveform parameter of each waveform may be adjusted to achieve substantially the same defibrillation efficacy for each electrical path. At least one waveform parameter of each waveform may be adjusted to achieve a selected current density distribution at the heart. At least one waveform parameter of each waveform may be adjusted to make the current density distribution at the heart more uniform than would be the case if the waveform parameter were the same for each of the electrical paths. The current density may be either peak or average current density. At least two electrodes positioned on the same side of the thorax may be combined into a unitary electrode pad that is adhered to and removed from the patient as one unit. There may be at least four electrodes, two on each side of the thorax, and two electrodes on each side of the thorax may each be combined into a unitary electrode pad that is adhered to and removed from the patient as one unit. The area of each of the electrodes through which the waveforms are delivered may be less than 70 percent of the projected area of the heart, and the sum of the areas of the electrodes on the same side of the thoracic cavity may be greater than 80 percent of the projected area of the heart. The determination of a transthoracic impedance distribution may occur at the time of or just prior to delivery of the defibrillation waveforms.

In a second aspect, the invention features a method of external electromagnetic stimulation of the interior of the body, the method comprising applying three or more electrodes to the exterior of the patient to establish at least two electrical paths across the interior of the patient, determining impedance information representative of an impedance distribution across the interior of the body, delivering an electromagnetic waveform across each of the at least two electrical paths, wherein at least one parameter of the waveform is selected using the impedance information to produce a selected current density distribution at one or more locations within the interior of the body.

Preferred implementations of this aspect of the invention may incorporate one or more of the following. The electromagnetic stimulation may be for defibrillation or cardioversion of the heart, the impedance distribution may be across the thorax, and the current density distribution may be at the heart. Determining impedance information may comprise electrical impedance tomography (EIT). Determining the impedance information may comprise imaging the body to determine positions of tissue regions, and computing the transthoracic impedance distribution from the positions of tissue regions and resistivities of the tissues. Imaging may comprise ultrasound imaging. The selected current density may be configured to deliver additional current density to selected myocardial regions expected to receive insufficient myocardial stimulation from a defibrillation shock. The selected myocardial regions may include an excitable gap region. The current density distribution may be selected using a model (e.g., a bidomain model) that predicts the regions expected to receive insufficient myocardial stimulation. The electromagnetic waveforms providing the selected current distribution may be delivered following a defibrillation pulse expected to deliver insufficient myocardial stimulation to the selected myocardial regions. ECG signals may be detected from a plurality of electrodes, and epicardial voltages may be estimated from the detected ECG signals. The one or more locations at which the selected current density distribution is produced may be areas of the heart, and the epicardial voltages may be used to determine the areas of the heart. Morphologies may be selected for the electromagnetic waveforms to produce the selected current density distribution at the areas of the heart. The areas of the heart may be areas in front of an advancing activation wavefront, and the selected current density distribution may be sufficient to quench the wavefront.

In a third aspect, the invention features a method of performing transthoracic defibrillation, comprising attaching three or more electrodes to the thorax of a patient to establish a plurality of electrical paths across the thoracic cavity and through the heart of the patient, and delivering a defibrillation waveform across each of at least two of the electrical paths, wherein the area of each of the electrodes through which the waveforms are delivered is less than 70 percent of the projected area of the heart, and the sum of the areas of the electrodes on the same side of the thoracic cavity is greater than 80 percent of the projected area of the heart.

Preferred implementations of this aspect of the invention may incorporate one or more of the following. The invention further comprises measuring an electrical, electrocardiographic, physiological, or anatomical parameter of the patient, and delivering defibrillation waveforms that under at least some circumstances may be different for different electrical paths, with at least one parameter of each waveform being dependent on the measured parameter. Measuring may comprise determining a transthoracic impedance distribution. The area of each of the electrodes through which the waveforms are delivered may be less than 60 percent of the projected area of the heart. The area of each of the electrodes through which the waveforms are delivered may be less than 50 percent of the projected area of the heart. The sum of the areas of the electrodes on the same side of the thoracic cavity may be greater than 90 percent of the projected area of the heart. The sum of the areas of the electrodes on the same side of the thoracic cavity may be greater than 100 percent of the projected area of the heart. The electrodes may be positioned in anterior and posterior locations, so that the electrical paths extend between the anterior and the posterior of the patient's thorax. The electrodes may be positioned at lateral locations, so that the electrical paths extend between left and right sides of the patient's thorax. The waveforms may be multiphasic. The waveforms may be monophasic. At least two of the electrodes may be combined in one unitary electrode pad that is applied and removed from a patient as a unit. There may be a seam line between areas of the pad in which electrodes are supported, with the seam line being constructed so that the pad can be folded without creasing the areas in which electrodes are supported. There may be a multiplicity of electrodes arranged on the unitary electrode pad. The multiplicity of electrodes may be arranged to increase packing density. The electrodes may be arranged in the form of a polygon tessellation. The tessellation may be a regular tessellation comprising regular polyhedra symmetrically tiling a plane. The polyhedra may be one of a triangle, square, or hexagon.

In a fourth aspect, the invention features a method of performing transthoracic defibrillation, comprising attaching three or more electrodes to the thorax of a patient to establish at least two electrical paths across the thoracic cavity and through the heart of the patient, delivering a biphasic or multiphasic defibrillation waveform across each of the at least two electrical paths, wherein under at least some circumstances the multiphasic waveforms delivered are different for the at least two electrical paths.

Preferred implementations of this aspect of the invention may incorporate one or more of the following. The invention further comprises determining a transthoracic impedance distribution across the at least two electrical paths, and delivering the biphasic or multiphasic waveforms with at least one parameter of each multiphasic waveform being dependent on the transthoracic impedance distribution. There may be two pairs of electrodes, with one electrode of each pair located on generally opposite surfaces of the thorax. One electrode of each pair may be located on the anterior and the posterior surfaces of the thorax. The invention further comprises a pair of bridge circuits, one bridge circuit for generating each of the biphasic or multiphasic waveforms. The biphasic or multiphasic waveforms may be delivered so as to overlap in time. The biphasic or multiphasic waveforms may be simultaneous. The biphasic or multiphasic waveforms may be sequential.

In a fifth aspect, the invention features a defibrillation electrode comprising a first electrical wire for conveying a defibrillation pulse to or from the electrode, a metallic layer connected to the electrical cable, a conductive, skin-contacting layer for conveying the pulse from the metallic layer to the skin, an ultrasound sensor, and a second electrical wire for connecting the ultrasound sensor to an ultrasound imaging circuit.

In a sixth aspect, the invention features a method of performing transthoracic defibrillation, comprising attaching three or more electrodes to the thorax of a patient to establish a plurality of electrical paths across the thoracic cavity and through the heart of the patient, using at least two different defibrillation circuits to generate at least two generally different defibrillation waveforms, delivering one of the at least two different defibrillation waveforms across each of the at least two electrical paths, and synchronizing delivery of the at least two defibrillation waveforms by communications between the at least two different defibrillation circuits.

Preferred implementations of this aspect of the invention may incorporate one or more of the following. The defibrillation circuits may each comprise a processor, an energy delivery circuit, and a switching circuit. The defibrillation circuits may be contained in separate housings, and the communications occurs between the housings. The switching circuit may be capable of generating a biphasic or multiphasic defibrillation waveform. The synchronizing delivering may include analog communication between the defibrillation circuits. The synchronizing delivering may include digital communication between the defibrillation circuits. The defibrillation circuits may be contained in separate housings. The defibrillation waveforms may deliver primarily electrical current. The defibrillation waveforms may deliver primarily a magnetic field. There may be an energy delivery circuit comprising one or more capacitors, a charging circuit for charging the one or more capacitors, and a switching circuit coupled to the one or more capacitors. An additional switch may be provided for decoupling the capacitor from the charging circuit prior to delivery of the waveform. The switching circuit may be configured as a Class D amplifier. The switching circuit may be configured as a Class B amplifier. The switching circuit may be configured as a Class AB amplifier. The invention further comprises delivering diaphragmatic stimulation. At least one diaphragmatic electrode may be provided for delivering the diaphragmatic stimulation. At least two of the defibrillation electrodes and at least one diaphragmatic electrode may be combined in one unitary electrode pad that is applied and removed from a patient as a unit. A device for delivering chest compressions may be provided. The device for delivering chest compressions may comprise a compression band surrounding the thorax. The device for delivering chest compressions may comprise a piston-driven device. A physiological parameter may be measured, and a prediction of defibrillation success based on analysis of the measured physiological parameter, and a coordinated delivery of defibrillation and chest compressions may be provided based on the prediction. The coordinated delivery of defibrillation and chest compressions may be manual, advisory, semi-automated, or fully automated. Diaphragmatic stimulation for assisted breathing may also be provided. Cardiac pacing may also be provided. Delivery of a second defibrillation waveform may be initiated after a delay interval following initiation of delivery of a first waveform. It has been found that delays in the range of 15-40 milliseconds result in an increase in the probability of refibrillation. The delay interval may be less than 15 milliseconds. Alternatively, the delay interval may be greater than 40 milliseconds but less than 200 milliseconds.

In a seventh aspect, the invention features a transthoracic defibrillator that comprises three or more electrodes configured to be attached to the thorax of a patient to establish at least two electrical paths across the thoracic cavity and through the heart of the patient; cables to connect at least some of the electrodes to a defibrillator circuit contained in a defibrillator housing, wherein the defibrillator circuit has the capability to deliver a first defibrillation waveform across a first electrical path and a second defibrillation waveform across a second electrical path, and wherein the locations and configurations of the electrodes and the first and second waveforms are configured so that the first waveform has a first current vector at the heart that is substantially aligned with the long axis of the fibers of a first portion of the heart and so that the second waveform has a second current vector at the heart that is substantially aligned with the long axis of the fibers of a second portion of the heart.

Preferred implementations of this aspect of the invention may incorporate one or more of the following. The defibrillator circuit may have the capability to make the first and second defibrillation waveform different from one another. A three-dimensional imaging method may be used to determine the orientation of the myocardial fibers. The imaging method (e.g., MRI) may include the capability of measuring current densities along with three dimensional volume images. Current may be injected during an MRI image generation by an external source to provide images of current flow in myocardial fibers. The defibrillator may be implanted, a first and second of the three or more electrodes may be provided by two separate housings each containing at least some defibrillator circuitry, the housings being electrically connected to one another, and a third and fourth of the three or more electrodes may be positioned outside the thoracic cage and connected electrically to one of the two separate housings. All of the electrodes used for delivering a defibrillation shock may be located outside the thoracic cavity. There may be a common electrical cable between the two separate housings, the common electrical cable comprising at least one conductor for carrying stimulation pulses to one of the electrodes and at least one conductor for carrying communications between the separate housings. The third electrode may comprise at least two intercostal electrodes electrically connected in common, with each intercostal electrode positioned in the vicinity of an intercostal space.

Among the many advantages of the invention (some of which may be achieved only in some of its various aspects and implementations) are that the invention can provide a transthoracic cardioversion/defibrillation system that results in reduced areal extent and effects of the excitable gap during defibrillation and provides improved efficacies relative to prior art. In some implementations, the excitable gap areal extant is reduced by increasing the combined area of the electrodes on each side of the thorax (e.g., making the combined area approximately equal to or larger than the area of the heart projected onto those electrodes). Because the transthoracic impedance varies considerably across the surface of the chest, affected by the bone, skeletal muscle and cartilage of the sternum and ribs and the disparate conductances of the myocardium, blood and lung, some implementations of the invention are capable of adjusting at least one of the parameters of the waveforms such as duration, waveform shape or amplitude based on a determination of the transthoracic impedance distribution. Such a determination might be as simple as an impedance measurement between the electrodes of the electrode pair, but might also include electrical impedance tomography, ultrasonic imaging or other imaging method to determine more accurate locations of the heart, lungs and skeleton. In some implementations, the variation in transthoracic impedance may be addressed by configuring the power sources delivering waveforms as independent current sources with the current set to a desired value across a range of physiological impedances.

Conductances at the body surface do not vary nearly as much as those of the internal organs, fluids, muscle and bone. Thus, the typical prior art single-point impedance measurement (e.g., at the body surface using the same electrodes that deliver the defibrillation current) is unable to estimate the impedance distribution within the thoracic cavity. Waveform shape, amplitude, or duration has been varied depending on such single-point impedance measurements, and this approach can have an impact on the efficacy of the defibrillation pulse, but its effect is limited by the fact that it does nothing to alter the current distribution in and around the heart. In preferred implementations, the invention determines the impedance (resistivity) distribution of the thorax in at least two dimensions, and uses the impedance distribution to determine the waveform parameters for each electrical path (current vector). E.g., the amplitude of the defibrillation pulse for each electrode pair can be independently adjusted to achieve a desired current distribution in and around the myocardium. Using such implementations of the invention, the current actually delivered to the organs themselves can be controlled at the surface of the body on as fine a level of detail as determined by the number, location and size of the electrodes located on the body surface.

Depending on the particular implementation, the invention is capable of improving the performance of any of the known types of defibrillation waveforms: monophasic, biphasic, or multiphasic. Preferably, the waveforms of the individual vectors are synchronized, but the invention is also capable of improving the performance of sequentially pulsed, multi-electrode defibrillation systems.

Some implementations of the invention measure the electrical, electrocardiographic, physiological, or anatomical parameters of the patient along an axis substantially similar to the axis of an electrode pair at the time of or just prior to defibrillation, and use the measurements to control the waveform parameters to improve efficacy.

Some implementations of the invention have current pathways that are independently measurable and controllable, but in other, simpler implementations, a waveform parameter of at least one of the current pathways is controlled as a function of the electrical, electrocardiographic, physiological or anatomical parameters of the patient.

Some implementations of the invention provide for synchronizing in a master/slave fashion multiple defibrillators that individually can function as standard monophasic or biphasic defibrillators.

The multiple electrodes may be implemented as active electrode areas integrated into a single pad, with one pad applied to each side of the thorax, thereby achieving a two-pad, easy-to-use system. The integrated pads may include anatomical markings such as correctly placed drawings of the sternum, sternal notch, or nipples to provide the clinician with the ability to more accurately place the electrodes on the patient. The electrodes may include sensors such as ultrasonic imaging, impedance, pulse oximetry, end-tidal carbon dioxide, blood pressure, velocity sensing, acceleration sensors.

The active electrode areas of the integrated pad may be configured to provide optimum spacing by placing them in a close-packed hexagonal, rectangular, or concentric configuration or other tessellations.

Other features and advantages of the invention will be apparent from the drawings, detailed description, and claims.

DETAILED DESCRIPTION

There are a great many possible implementations of the invention, too many to describe herein. Some possible implementations that are presently preferred are described below. It cannot be emphasized too strongly, however, that these are descriptions of implementations of the invention, and not descriptions of the invention, which is not limited to the detailed implementations described in this section but is described in broader terms in the claims.

Figure 1:
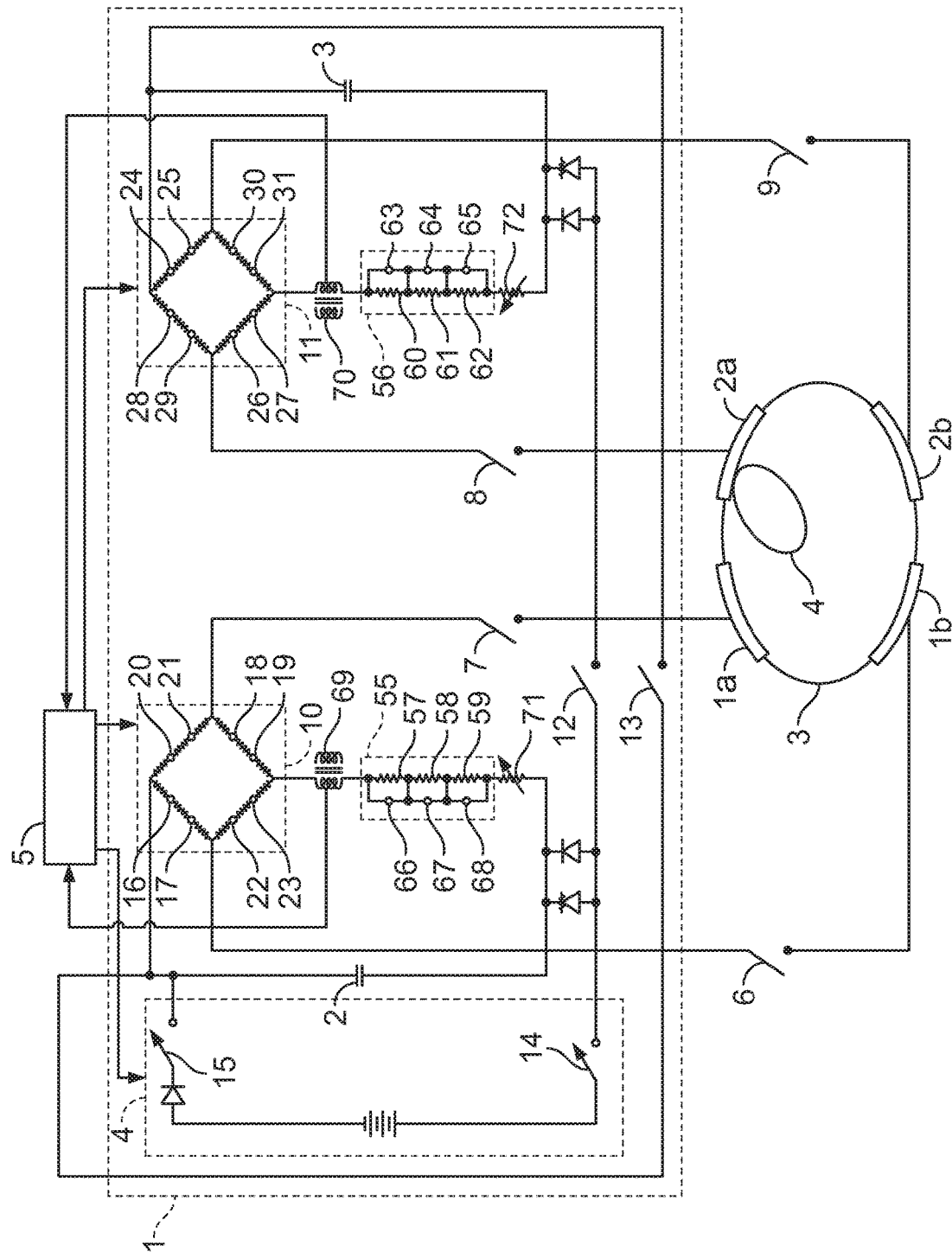
FIG. 1 is a schematic of the circuitry for a biphasic defibrillator implementation.

One implementation of the invention is depicted in FIG. 1. The defibrillation waveform delivered to the patient is a biphasic or multiphasic waveform as described in U.S. Pat. No. 6,096,063. As described in that patent, the electromagnetic (EM) energy delivery means 1 is comprised of storage capacitors 2, 3 which are charged to a therapeutically effective voltage by a charging circuit 4 under control of the processing means 5 while relays 6, 7, 8 and 9 and the H-Bridges 10, 11 are open. As a means of reducing both size and cost, charging circuit 4 is used to charge both storage capacitors 2, 3 simultaneously. The first electrode pair 1 and the second electrode pair 2 are self adhesive pads, such as STAT-PADZ (ZOLL Medical Chelmsford Mass.), that are adhered to the patient's chest 3, shown in cross-section in FIG. 1.

Figure 2:
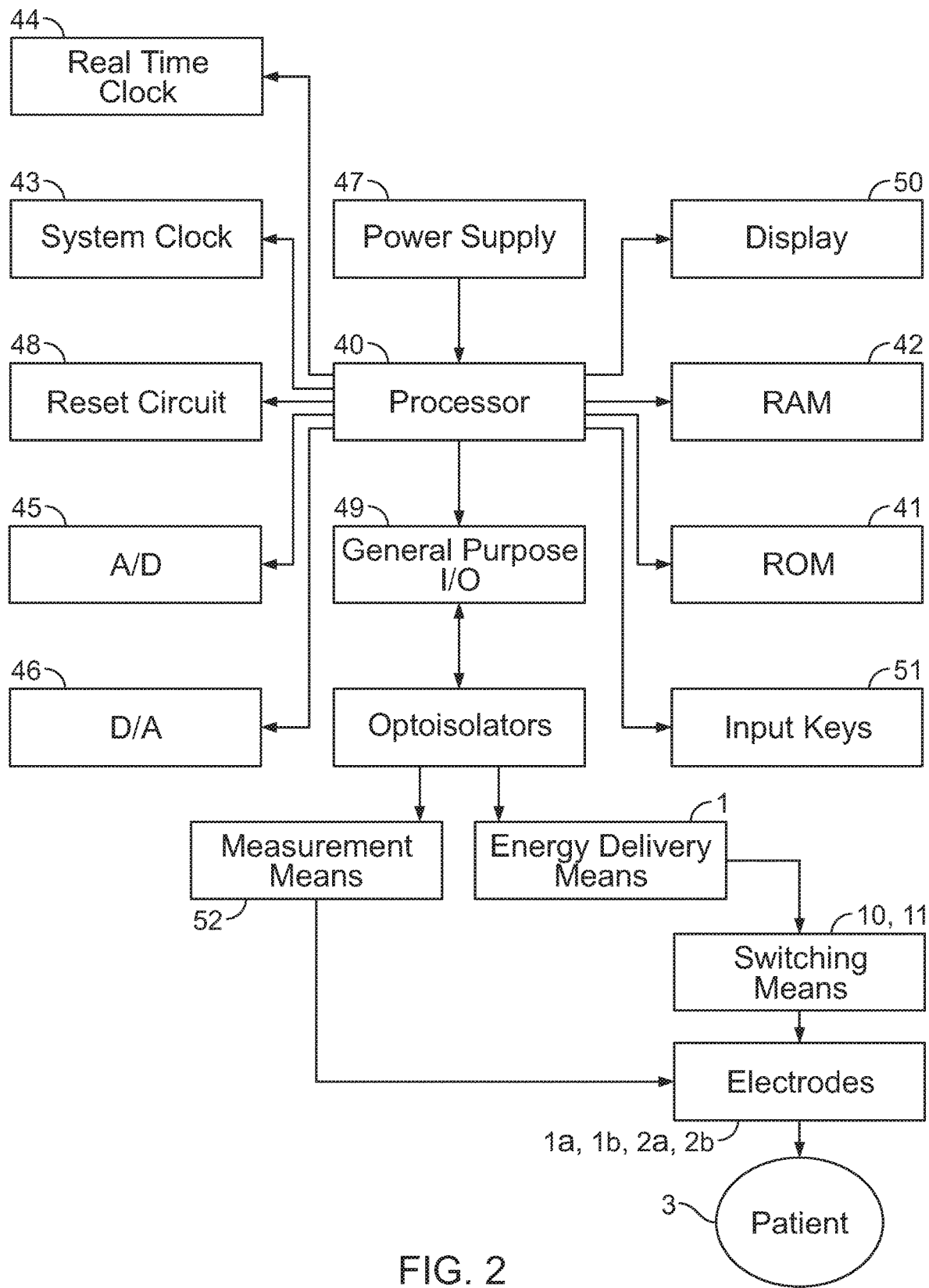
FIG. 2 is a block diagram of the implementation of FIG. 1.

Upon determination by processing means 5, using any existing methods known to those skilled in the art, of the appropriate time to deliver the defibrillation energy to the patient, relay switches 12, 13, 14 and 15 are opened, and relay switches 6, 7, 8 and 9 are closed. Then, the electronic switches 16, 17, 18, and 19 of H-bridge 10 and 24, 25, 26, and 27 of H-bridge 11 are closed to allow electric current to pass through the patient's body in one direction, after which electronic switches 16, 17, 18, and 19 of H-bridge 10 and 24, 25, 26, and 27 of H-bridge 11 are opened and 20, 21, 22, and 23 of H-bridge 10 and 28, 29, 30 and 31 of H-bridge 11 are closed to allow the electric current to pass through the patient's body in the other direction. Relay switches 12, 13, 14 and 15 are combined in double-pole double-throw configuration (DPDT) to reduce size and cost. DPDT relay 12, 13 serves the purpose of isolating the current sources for the electrode pairs during discharge. Electronic switches 16-31 are controlled by signals from respective opto-isolators, which are, in turn, controlled by signals from the processing means 5. As shown in FIG. 2, processing means 5 is preferably a microprocessor, such as a Hitachi SH-3 40 combined with a read only memory device (ROM) 41, random access memory (RAM) 42, Clock 43, real time clock 44, analog-to-digital 45 and digital-to-analog 46 converters, power supply 47, reset circuit 48, general purpose input/output 49, and user interface in the form of a display 49 and input keys 50 and other circuitry known to those skilled in the art. A measurement means 52 is provided for measurement of electrical, electrocardiographic, physiological or anatomical parameters of the patient, the processing means 5 controlling the waveform parameters of at least one of the discharge pathways based on this measurement. Relay switches 6, 7, 8, and 9 which are also controlled by the processing means 5, isolate patient 3 from leakage currents of H-bridge switches 16-31 which may be about 500 microamperes.

Resistive circuits 55, 56 that include series-connected resistors 57, 58, 59 and 60, 61, 62, respectively, are provided in the current path, each of the resistors being connected in parallel with shorting switch 63-68 controlled by processing means 5. The resistors are preferably of unequal value and stepped in a binary sequence such that with the various combinations of series resistance values, there are $2^n$ different combinations, where n is the number of resistors. Immediately prior to delivering the therapeutic defibrillation energy a smaller amplitude "sensing" pulse is delivered by closing H-bridge switches 16-19 and 24-27 and the resistor shorting switches 63-68 are all open so that current passes through the resistors in series. The current sensing transformers 69 and 70 sense the current that passes through the patient through their respective electrode pairs 1a, 1b, 2a and 2b, from which the processing means 5 determines the resistance of the patient 3.

The initial sensing pulse is integral with, i.e., immediately followed by, a biphasic defibrillation waveform, and no re-charging of storage capacitor occurs between the initial sensing pulse and the biphasic defibrillation waveform. If the patient resistance sensed during the initial sensing pulse is low, all of the resistor-shorting switches 63-68 are left open at the end of the sensing pulse so that all of the resistors 57-62 remain in the current path (the resistors are then successively shorted out during the positive phase of the biphasic defibrillation waveform in the manner described below in order to approximate a rectilinear positive phase). Thus, the current at the beginning of the positive first phase of the biphasic defibrillation waveform is the same as the current during sensing pulse. If the patient resistance sensed during the sensing pulse is high, some or all of the resistor-shorting switches 63-68 are closed at the end of the sensing Pulse, thereby shorting out some or all of the resistors.

Thus, immediately after the sensing pulse, the biphasic defibrillation waveform has an initial discharge current that is controlled by microprocessor 46, based on the patient impedance sensed by current-sensing transformer 69, 70. The current level of the sensing pulse is always at least 50 percent of the current level at the beginning of positive first phase, and the sensing pulse, like the defibrillation pulse, is of course a direct-current pulse.

By appropriately selecting the number of resistors that remain in the current path, the processing means reduces (but does not eliminate) the dependence of peak discharge current on patient impedance, for a given amount of charge stored by the charge storage device. For a patient impedance of 15 ohms, the peak current is about 25 amperes, whereas for a patient impedance of 125 ohms, the peak current is about 12.5 amperes (a typical patient is about 75 ohms.)

During the positive phase of the biphasic waveform, some or all of the resistors 57-62 that remain in series with the patient 3 are successively shorted out. Every time one of the resistors is shorted out, an upward jump in current occurs in the waveform, thereby resulting in the sawtooth ripple shown in the waveform of FIG. 3. The ripple tends to be greatest at the end of the rectilinear phase because the time constant of decay (RC) is shorter at the end of the phase than at the beginning of the phase. Of course, if all of the resistors have already been shorted out immediately after the end of the sensing pulse, the positive phase of the biphasic waveform simply decays exponentially until the waveform switches to the negative phase.

Figure 3:
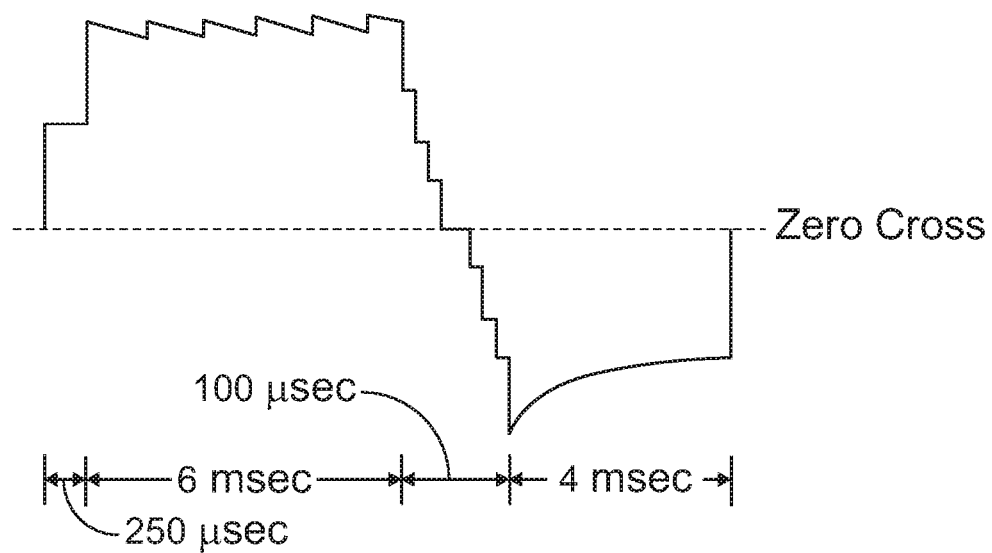
FIG. 3 is a plot of a biphasic waveform produced by the implementation of FIG. 1.

As is shown in FIG. 3, at the end of the positive phase, the current waveform decreases through a series of rapid steps from the end of the positive phase to the beginning of negative phase, one of the steps being at the zero crossing. Processing means 5 accomplishes this by (1) successively increasing the resistance of resistive circuit 55, 56 in fixed increments through manipulation of resistor-shorting switches 57-62, then (2) opening all of the switches in H-bridges 10-11 to bring the current waveform down to the zero crossing, then (3) reversing the polarity of the current waveform by closing the H-bridge switches that had previously been open in the positive phase of the current waveform, and then (4) successively decreasing the resistance of resistance circuit 55, 56 in fixed increments through manipulation of resistor-shorting switches 57-62 until the resistance of resistance circuit 55, 56 is the same as it at the end of the positive phase.

In one implementation a variable resistor 71, 72 is provided in series with the other resistors 57-62 to reduce the sawtooth ripple. Every time one of the fixed-value resistors 57-62 is shorted out, the resistance of variable resistors 71, 72 automatically jumps to a high value and then decreases until the next fixed-value resistor is shorted out. This tends, to some extent, to smooth out the height of the sawtooth ripple from about 3 amps to about 0.1 to 0.2 amps, and reduces the need for smaller increments of the fixed-value (i.e., it reduces the need for additional fixed-value resistor stages).

Figure 4:
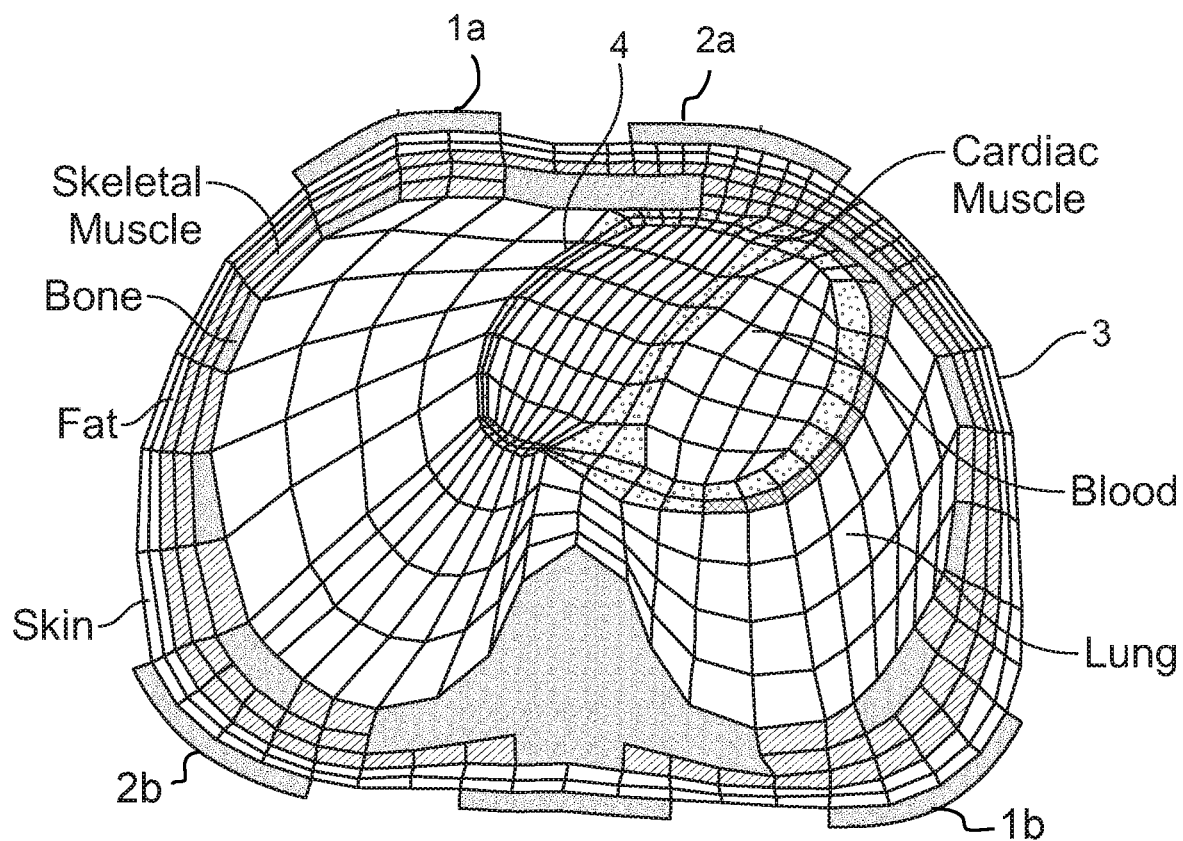
FIG. 4 is a cross section of the thorax at the elevation of the heart used in finite element modeling showing the finite element mesh decomposition.

A cross-sectional view of the human thorax is shown in FIG. 4. Each of the constituent tissues are subdivided into cells for use in finite element simulations of the fields and currents generated by defibrillation pulses. Electrode pairs 1a, 1b, 2a, and 2b are also depicted in the figure. FIG. 5a-d depicts a simplified version of the cross section of FIG. 4. A line is defined in the figure, the Cardiac Center of Mass (CCOM) line 75, which runs through the CCOM point 76 and is parallel to the patient's back. In preferred implementations, at least one, and preferably two, electrodes are located posterior to the CCOM line. Additionally, the midpoint/COM (MCOM) line 77 is the line defined by midpoint of the lateral extent (MLE) of the posterior electrode or electrodes 78, 79 and the CCOM point 76. The electrode plane 81, is defined by the plane resulting in the least mean squared error distance to the centroids 82 of the electrodes distal 84 to the MLE 78. There is further defined a Projected Cardiac Area (PCA), that is the area in the electrode plane 81 of the shape formed by the intersection of the electrode plane 81 with the locus of lines 80 parallel to the MCOM line 77 and tangent to the surface of the heart 83. The area, shape and position of the electrodes are such that the area of each individual electrode is less than 70% of the PCA and the sum of the areas of the electrodes distal 84 to the MLE 78 is greater than 80%, and preferably 100%, of the PCA.

Figure 5A:
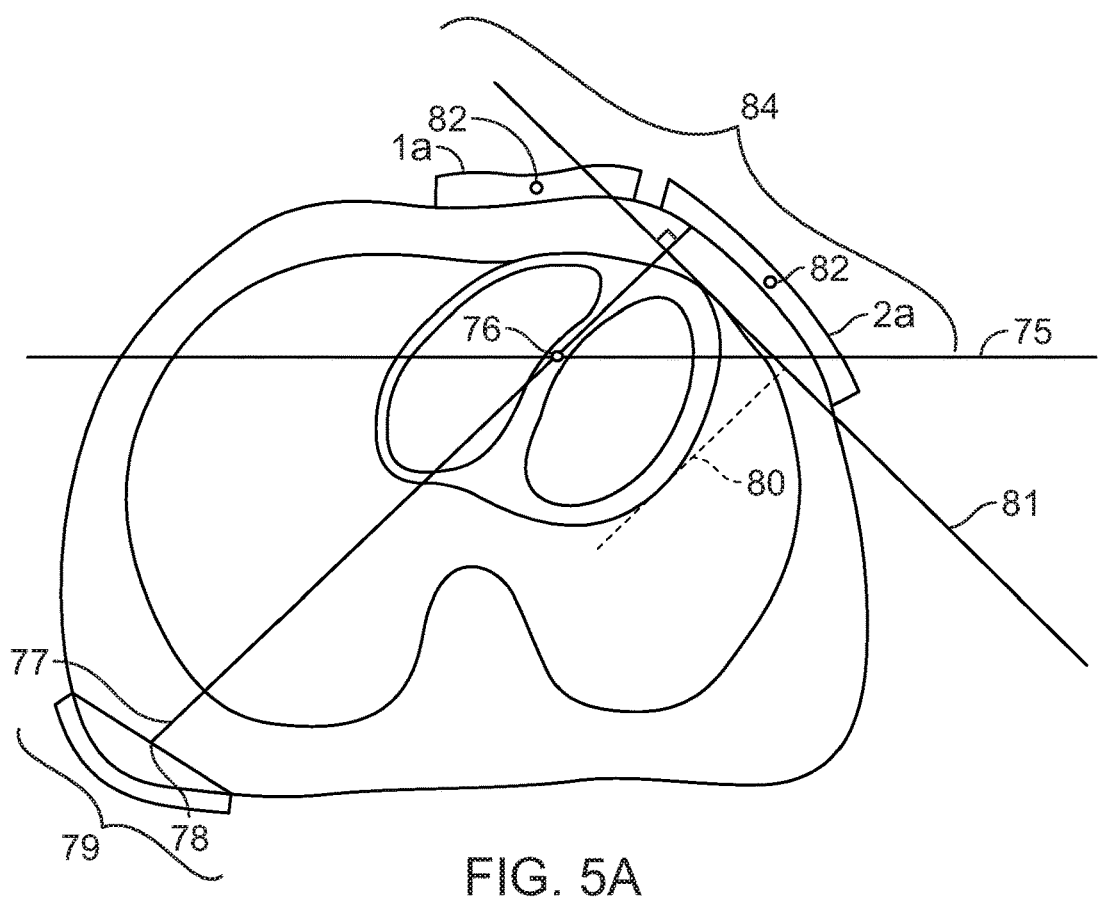
FIG. 5a is a simplified version of FIG. 4 with electrode locations and coordinate axes and plans.
Figure 5B:
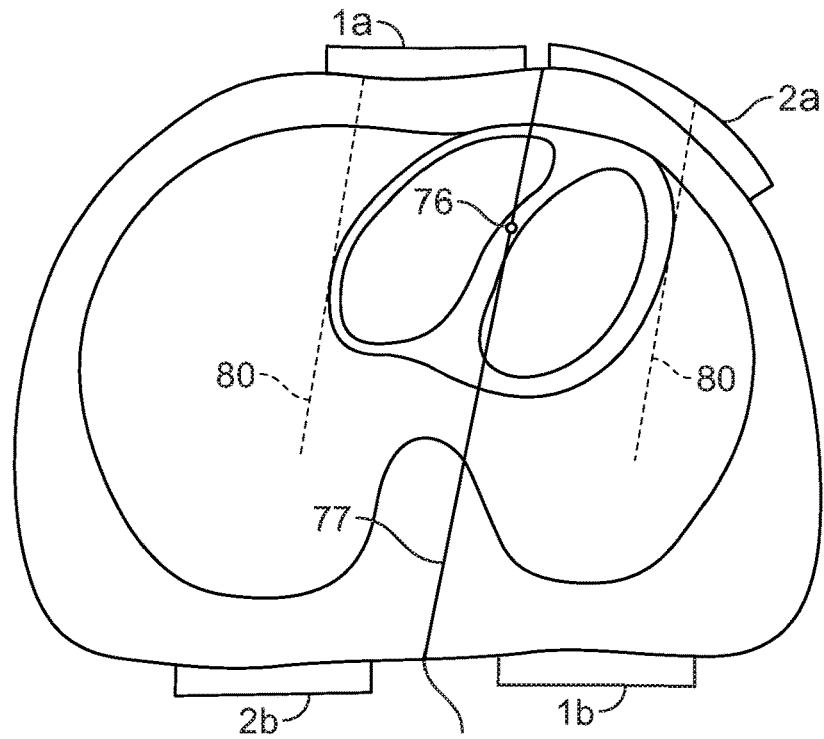
FIG. 5b is a simplified version of FIG. 4 showing a preferred set of electrode locations.
Figure 5C:
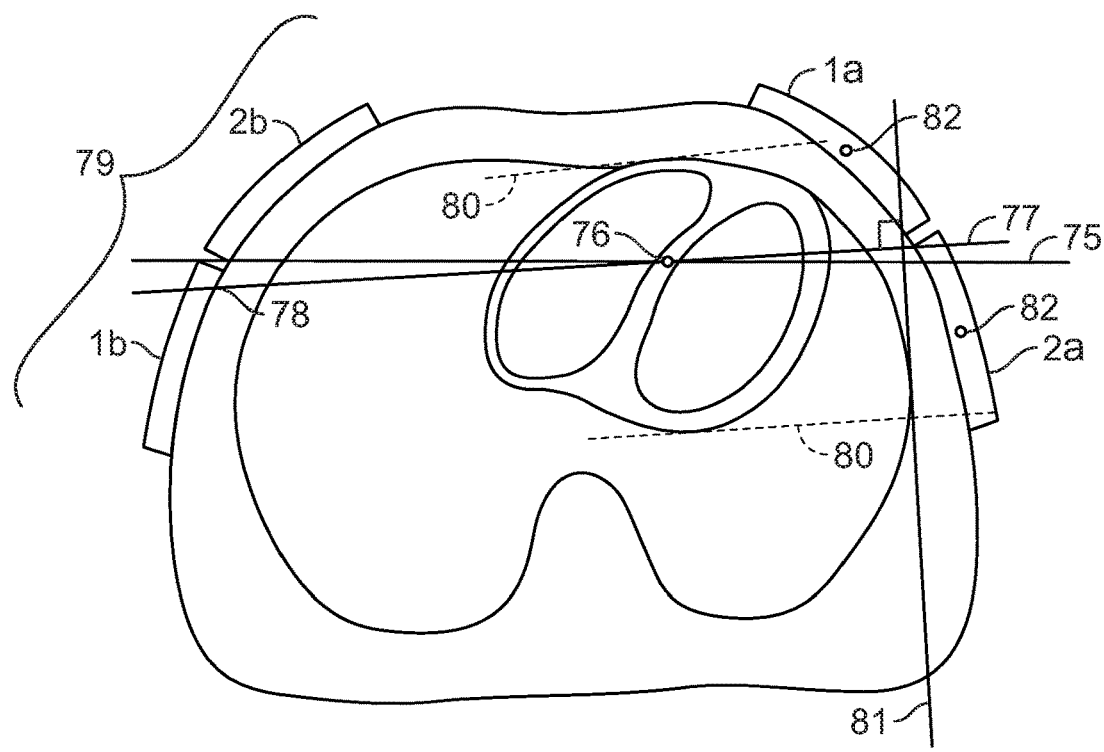
FIG. 5c is a simplified version of FIG. 4 showing an alternative set of electrode locations.
Figure 5D:
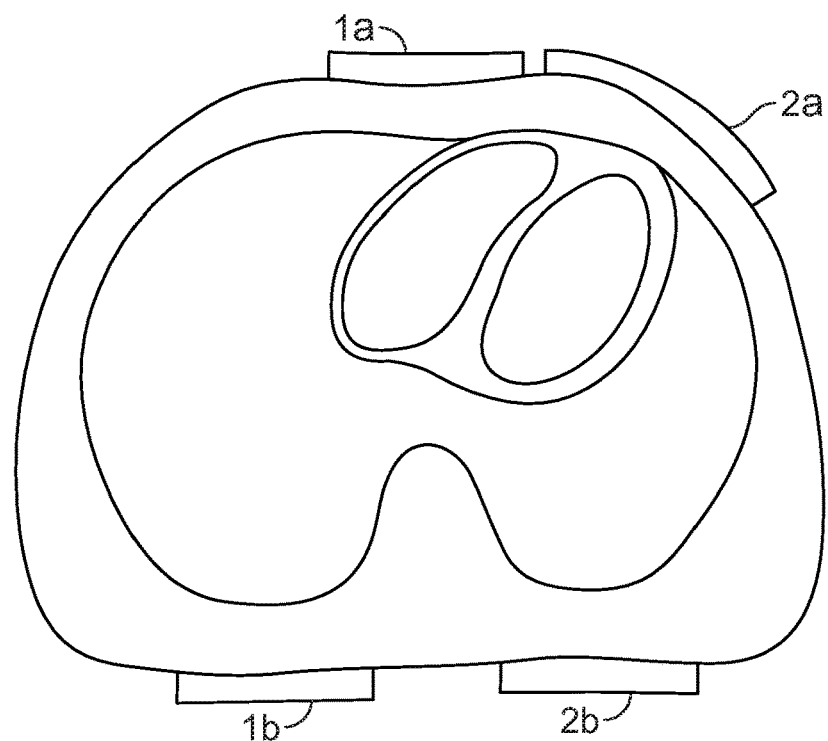
FIG. 5d is a simplified version of FIG. 4 showing a further alternative set of electrode locations.
Figure 7:
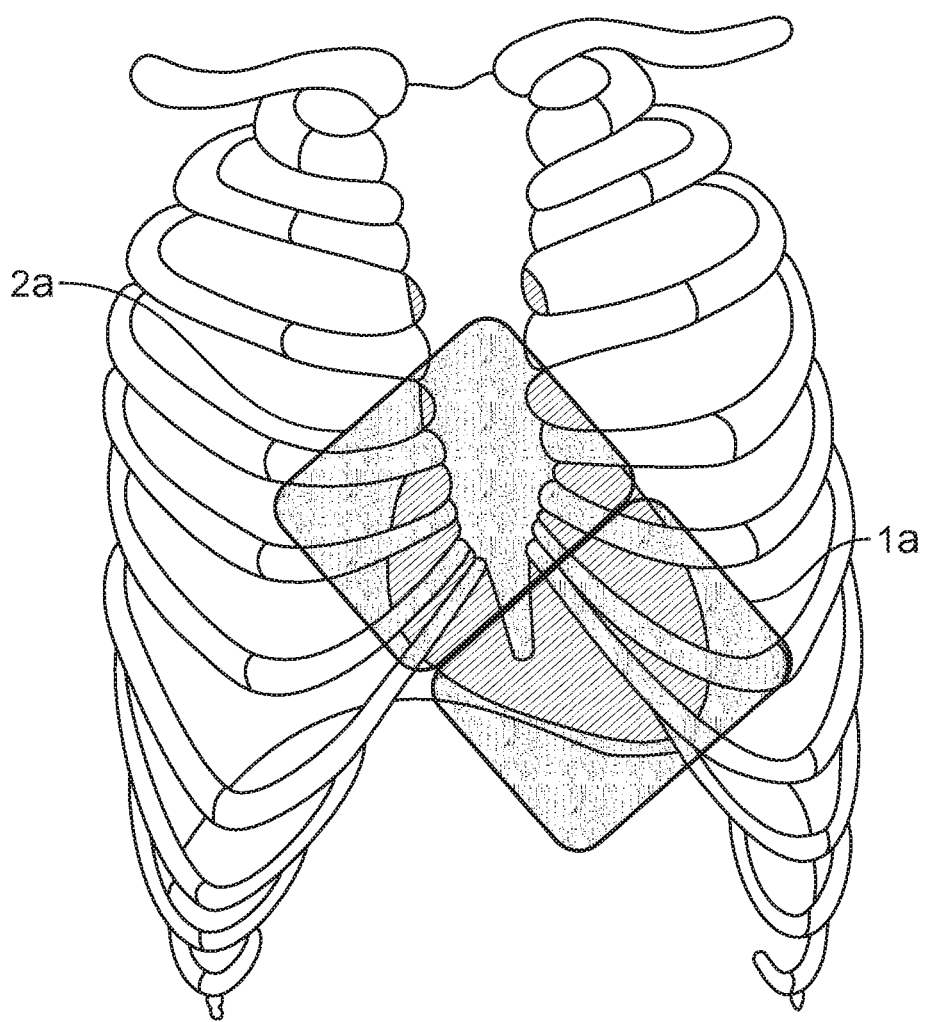
FIG. 7 shows the placement of the anterior electrodes of FIG. 5b relative to the heart.
Figure 8A:
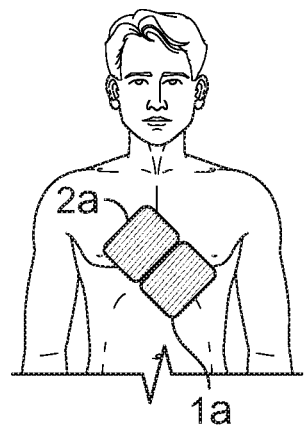
FIGS. 8a and 8b show the placement of the electrodes of FIG. 5b.
Figure 8B:
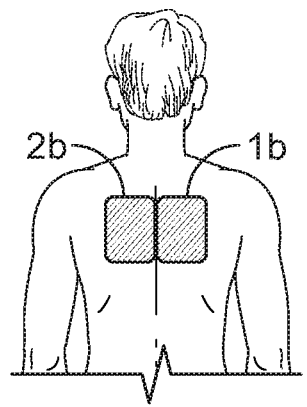
Figure 9:
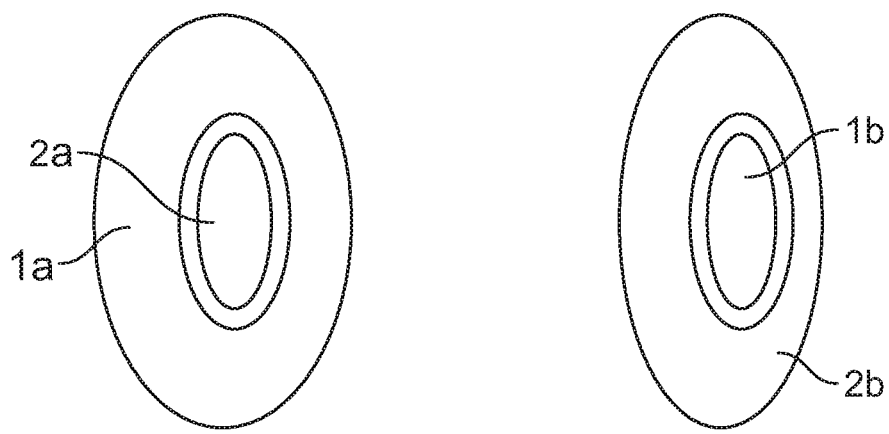
FIG. 9 shows an example of an annular electrode configuration.

In a preferred implementation, the electrodes are positioned as shown in FIGS. 5b, 7, 8a and 8b. FIG. 7 shows the relative location of the electrodes 1a, 2a and the thoracic cage and the heart 4. FIGS. 8a and 8b show the electrode placement on a typical patient. FIG. 5c depicts a lateral placement of the electrode pairs. In another implementation, the electrodes may be so configured as concentric, as shown in FIG. 9. The electrodes may also be placed so that the current pathways are essentially parallel, as shown in FIG. 5d (in which the locations of electrodes 1b and 2b have been reversed from FIG. 5b).

The conductances of the various tissues as shown in FIG. 4 are approximately as follows:

| Tissue type | Conductivity (ohms-cm) |
|---|---|
| Skin | 3.4 |
| Blood | 6.5 |
| Lung | 0.7 |
| Skeletal Muscle | 1.5 (transverse) |
| | 4.2 (longitudinal) |
| Fat | 0.5 |
| Cardiac Muscle | 7.6 |
| Bone | 0.06 |

Conductivities of the various tissues can vary by as much as a factor of 100. To accommodate this, waveform parameters of the energy delivered to each of the discharge pathways is independently controllable. For example, this may be accomplished in the just-described implementation by providing two high voltage capacitors 2, 3 and by appropriately switching the resistors 57-62 that remain in series with the patient 3. By appropriately selecting the number of resistors that remain in the current path, the dependence of peak discharge current on patient impedance can be reduced (but not eliminated), for a given amount of charge stored by the charge storage device. For example, for a patient impedance of 15 ohms, the peak current is about 25 amperes, whereas for a patient impedance of 125 ohms, the peak current is about 12.5 amperes (a typical patient is about 75 ohms.)

Alternatively, independent control may also be achieved by providing only one high voltage capacitor for more than one of the electrode pairs while still providing separate resistor networks 57-59 and 60-62 for each current pathway. Another waveform parameter that may be adjusted is waveform duration, which is controllable by switch networks 10, 11. The average first phase current can also be independently adjusted, e.g., by providing a second charging circuit 4 to charge a second group of one or more capacitors to a voltage independent from the first group of one or more capacitors. Waveform parameters for independent adjustment include, but are not limited to, tilt, duration, first phase duration, second phase duration, current, voltage, and first phase average current.

Figure 6:
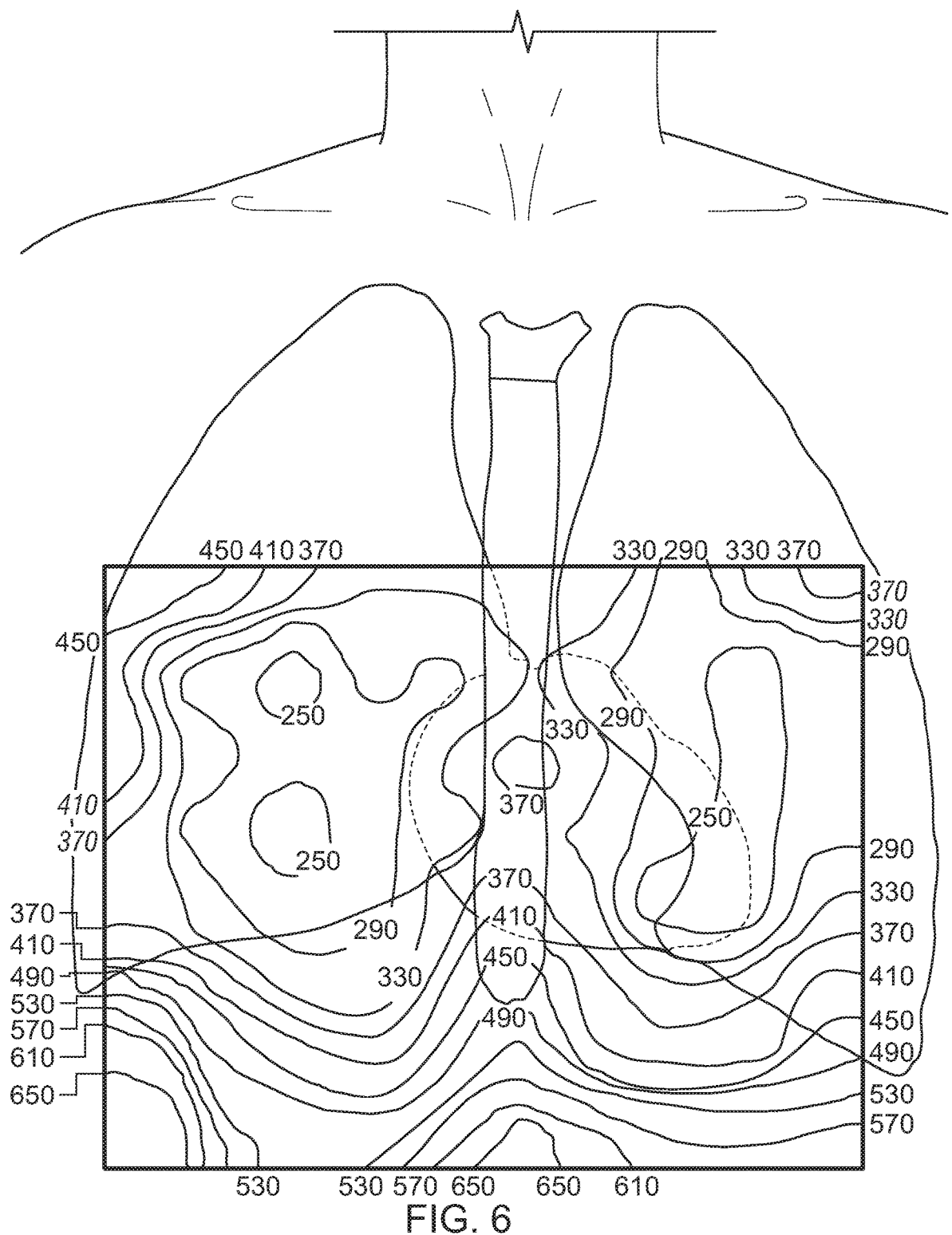
FIG. 6 shows an isoconductance plot of the anterior thorax.

As can be seen in the isoadmittance curves shown in FIG. 6, the conductances of the internal organs, muscle and bone vary significantly, much more so than do conductances at the body surface. In a preferred implementation, electrical impedance tomography (EIT) is used to determine these internal conductances or impedances. Electrical impedance tomography (EIT) is used to determine the resistivity distribution of the thorax in at least two dimensions, and the calculated resistivity distribution is then used to determine the waveform parameters for each current vector. For example, the amplitude of the defibrillation pulse for each electrode pair can be independently adjusted to achieve the optimal current distribution in and around the myocardium. Using such a method, the current actually delivered to the organs themselves can be controlled at the surface of the body on as fine a level of detail as determined by the number, location and size of the electrodes located on the body surface.

In the most basic implementation, only three electrodes with three possible electrode pairs is sufficient to use EIT methods to determine waveform parameters. In the preferred implementation shown in FIG. 5b, four electrodes are used, for a total of six [(n−1)!] possible electrode pairs. This number is chosen for ease of implementation and cost; implementations with more electrode pairs are possible.

The EIT system is governed by Poisson's equation:

$$\nabla \cdot \rho^{-1} \nabla V = I,$$

Where V is the voltage, $\rho$ is the resistivity distribution and I is the impressed current source distributions within the region being studied and the boundary conditions are $V_0$ and $J_0$. In the case of EIT, high frequency, low amplitude signals, e.g., 60 KHz and ~1 microampere respectively, are used. Since there are no current sources of this frequency in the body, then $\rho=0$, and Poisson's equation becomes Laplace's equation:

$$\nabla \cdot \rho^{-1} \nabla V = 0$$

In the field of EIT, several types of problems are studied:
1. The "forward problem", where $\rho$, $V_0$ and $J_0$ are given and the goal is to determine the voltage and current distributions V and J.
2. The "inverse problem", where V and J are given and the goal is to determine $\rho$.
3. The "boundary value" problem where $V_0$ and $J_0$ are given and the goal is to determine $\rho$, V and J.

In a preferred implementation, $\rho$, V and J are determined using boundary value problem methods, then once $\rho$ is determined, the optimal $V_0$ and $J_0$ are determined using a modified inverse problem where the desired V and J in and near the myocardium are given and the defibrillation waveforms for each of the electrode pairs is generated.

In general principle, the process of EIT involves injecting a current by an electrode, and the induced voltage is measured at multiple points on the body surface. In the preferred implementation, what is termed the "multireference method" is used for configuring the current voltage pairs. (Hua P, Webster J G, Tompkins W J 1987 Effect of the Measurement Method on Noise Handling and Image Quality of EIT Imaging, Proc. Annu. Int. Conf. IEEE Engineering in Medicine and Biology Society 9 1429-1430.) In the multireference method, one electrode is used as the reference electrode while the remaining electrodes are current sources with the induced voltages being measured on each electrode simultaneously while the current is being delivered. The amplitude of the current sources are individually varied and each electrode is treated as a reference lead in succession. Finite element methods are then used to convert the calculus problem ($\nabla \cdot \rho^{-1} \nabla V = 0$) into a linear algebra problem of the form YV=C, where Y, V, and C are the conductance, voltage, and current matrices respectively. Y, V, and C are also sometimes known as the master matrix, node voltage vector, and node current vector respectively. Mesh generation is performed on the two or three-dimensional physical model with triangular or quadrilateral elements for two dimensional problems and hexahedral shapes for three-dimensional problems. Boundary conditions are then set such as at the reference node or driving electrodes for Dirichlet (known surface voltages) or Neuman (known surface currents) boundary conditions. A number of methods have been used to compute the master matrix such as Gaussian elimination or Cholesky factorization.

The Newton-Raphson algorithm may also be used for reconstruction of the resistivity distribution. The algorithm is an iterative algorithm particularly well suited to non-linear problems. The Newton-Raphson method minimizes an error termed the "objective function". Here, it is defined as the equally weighted mean square difference between the measured and estimated voltage responses:

$$\Phi(\rho) = (\frac{1}{2})(V_e(\rho) - V_0)^T (V_e(\rho) - V_0).$$

Using methods known to those skilled in the art, an algorithm is utilized whereby a distribution is first estimated, then the theoretical voltage response to a given current input is calculated using the finite element method. The estimated voltages are subtracted from the measured voltages to obtain the objective function. If the objective function is less than an error threshold, the estimated distribution is deemed to be an acceptable estimation. If not, the following equation is used to update the resistivity distribution:

$$\Delta \rho^k = -[V_e(\rho^k)^T V_e'(\rho^k)]^{-1} \{V_e'(\rho^k)^T [V_e'(\rho^k) - V_0]\}$$

This sequence is repeated until an acceptable estimation is achieved.

Figure 21:
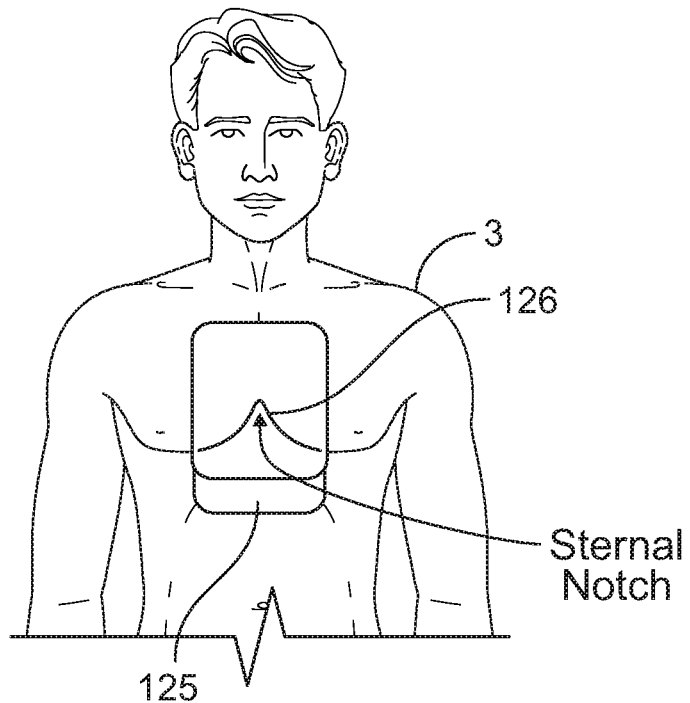
FIG. 21 is a perspective view of a patient to which an integrated defibrillation pad with anatomical markings has been applied.

In a preferred implementation, a table lookup method is provided to determine the estimated voltage matrix $V_e(\rho)$. The table values are based on average patient resistivity distributions and assuming correct placement of the electrode. Better accuracy can be achieved by providing anatomical markings 126 on the electrode pad as shown in FIG. 21.

Accuracy may also be improved by providing a secondary imaging method such as ultrasound to take advantage of its higher imaging resolution to calculate the positions of the internal organs relative to the electrodes. If a secondary imaging method such as ultrasound is used to determine the positions of internal tissues, EIT can be used to determine the resistivities of each tissue type.

In other implementations, an average resistivity value is determined for the tissue regions as defined by the secondary imaging method. This is accomplished by first defining a tissue region such as the lungs or myocardium by standard image processing methods. Next, the calculated resistivity distribution is overlayed onto the secondary image. All nodes of the resistivity distribution that are contained within a particular tissue region are combined together into a single resistivity measure for that tissue region. The method of combination may be an averaging, median, or other statistical or image processing method.

The optimal $V_0$ and $J_0$ are determined using a modified inverse problem where the desired V and J in and near the myocardium are given and the defibrillation waveforms for each of the electrode pairs is generated.

Figure 10:
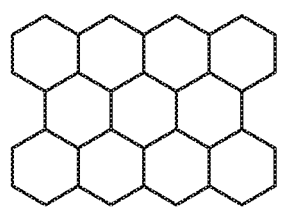
FIG. 10 shows examples of electrodes arranged in regular tessellations.
Figure 10:
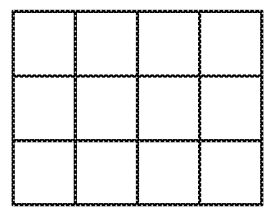
Figure 10:
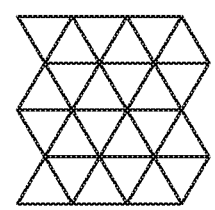
Figure 11:
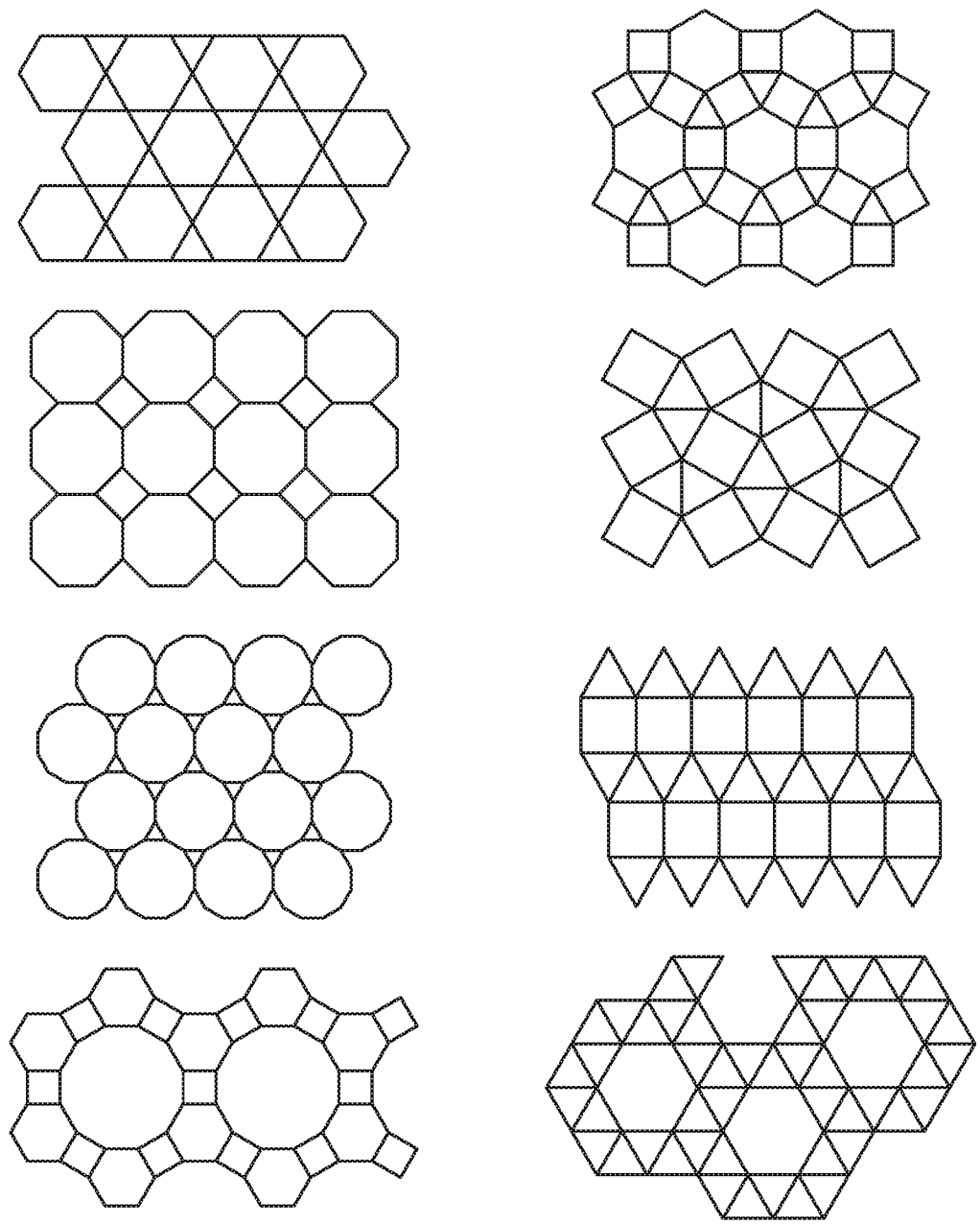
FIG. 11 shows examples of electrodes arranged in semi-regular tessellations.
Figure 12:
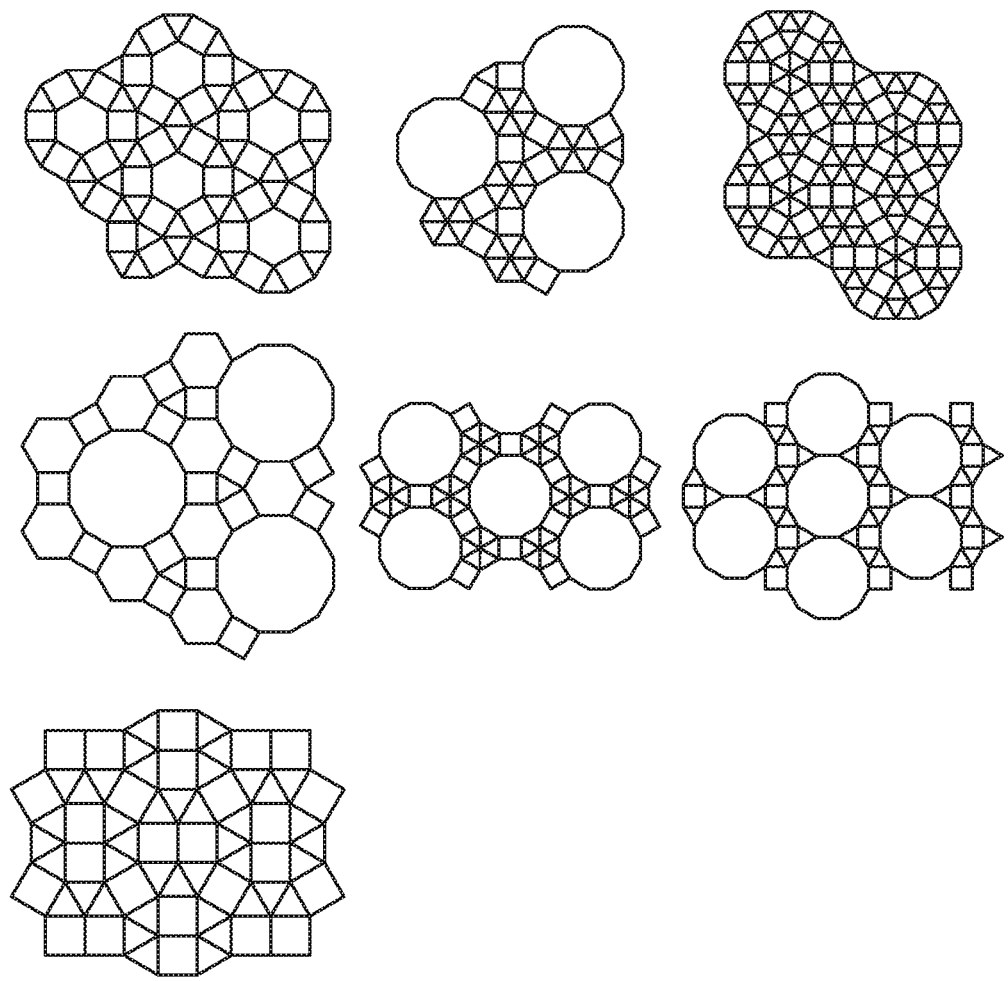
FIG. 12 shows examples of electrodes arranged in demi-regular tessellations.

Improved current delivery (and impedance measurements) can be achieved by close-packing a large number of electrodes. Many arrangements of electrodes are possible. In a preferred implementation, the configuration of electrodes is determined with the assistance of the theory of tessellation. A regular tiling of polygons (in two dimensions), polyhedra (three dimensions), or polytopes (n dimensions) is called a tessellation. Tessellations can be specified using a Schläfli symbol. The breaking up of self-intersecting polygons into simple polygons is also called tessellation, or more properly, polygon tessellation. There are exactly three regular tessellations composed of regular polyhedra symmetrically tiling the plane, as shown in FIG. 10. Tessellations of the plane by two or more convex regular polygons such that the same polygons in the same order surround each polygon vertex are called semi-regular tessellations, or sometimes Archimedean tessellations. In the plane, there are eight such tessellations, shown in FIG. 11. There are fourteen demi-regular (or polymorph) tessellations, which are orderly compositions of the three regular and eight semi-regular tessellations. These polyhedra are shown in FIG. 12. Other demi-regular tessellations are Penrose Tilings. In three dimensions, a polyhedron that is capable of tessellating space is called a space-filling polyhedron. Examples include the cube, rhombic dodecahedron, and truncated octahedron. There is also a 16-sided space-filler and a convex polyhedron known as the Schmitt-Conway polyhedron, which fills space only aperiodically. Space-filling polyhedron can be utilized to better fit the electrodes to the three-dimensionality of the human thorax. In the preferred implementation, the electrode tessellation pattern is a cubic or hexagonal regular tessellation.

Figure 24A:
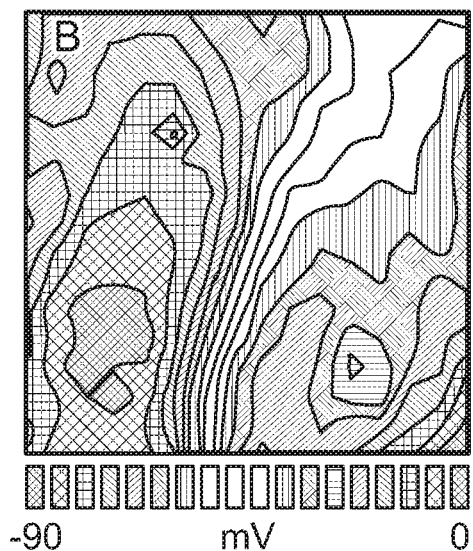
FIGS. 24A and 25A show two different examples of the spatial distribution of epicardial voltages across a region of the heart immediately subsequent to defibrillation shock. Different shades of gray represent different voltage levels, with the darkest region at −90 mV (−50 mV in FIG. 25A) at the extreme left in the figure indicating the region of greatest depolarization, and the darkest region at 0 mV (+10 mV in FIG. 25A) at the extreme right indicating the region of greatest hyperpolarization. The white region and the bands immediately adjacent are the excitable gap. Isopotential contour lines are drawn 5 mV apart on the basis of the assumption that the normal resting potential is 285 mV and action potential amplitude is 100 mV.
Figure 24B:
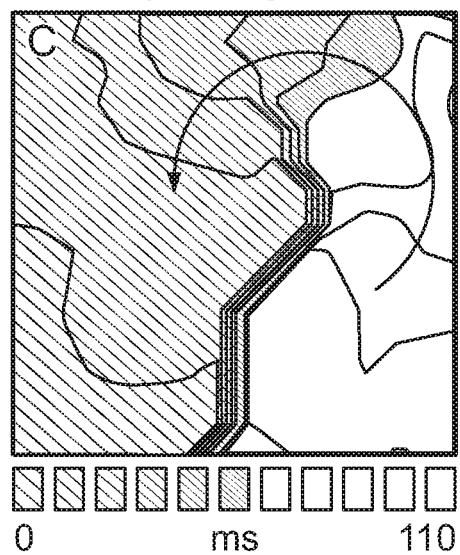
FIGS. 24B and 25B show two different examples of the spatial distribution of epicardial phase across a region of the heart immediately following a defibrillation shock. Different shades of gray represent different isochronous regions (i.e., regions at approximately the same cardiac phase). The regions are 10 msec apart, with the region in white representing the time immediately after the defibrillation shock (0 msec), and the region in the darkest gray representing 120 msec after the shock.
Figure 24C:
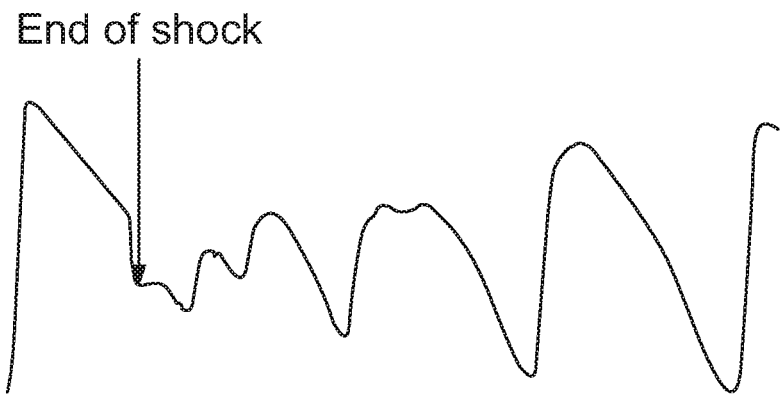
FIGS. 24C and 25C are ECG signals representing possible behavior immediately after a defibrillation pulse, and show onset of tachycardia.
Figure 25A:
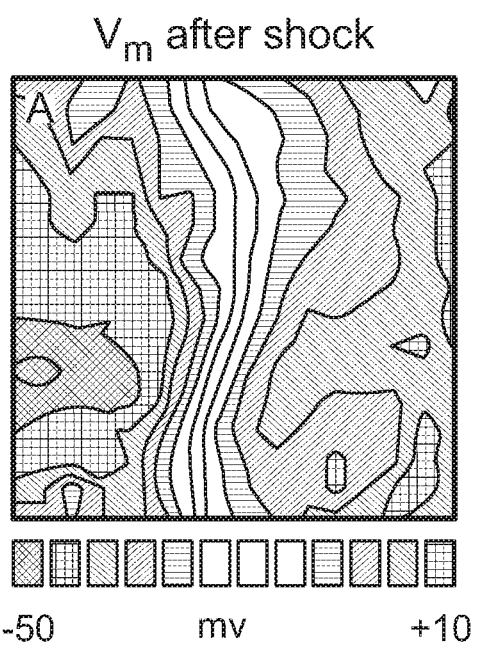
Figure 25B:
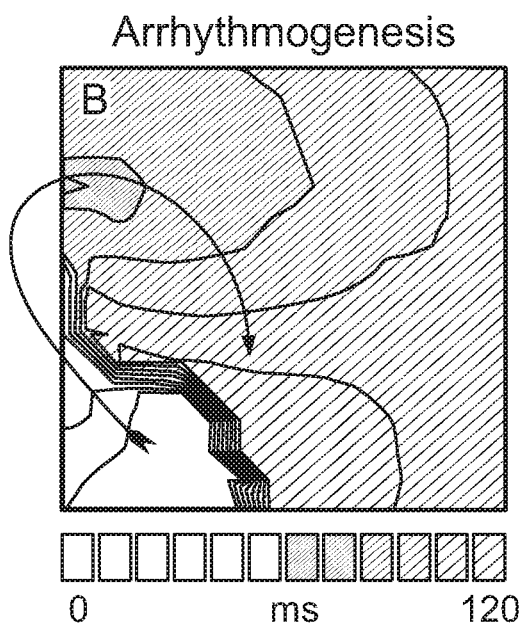
Figure 25C:
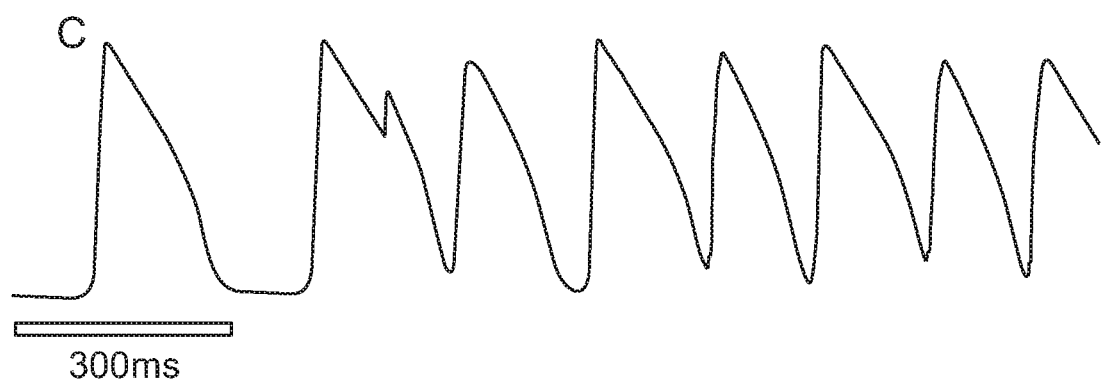

In another implementation, using the previously-described EIT methods, it is possible to deliver arbitrarily complex spatial and temporal distributions of current to the heart limited only by the number and size of electrodes on the thorax. During fibrillation, either pre or post-shock, the direction of the activation wavefront can vary and is not predictable, as is the case with a normal sinus rhythm. In FIG. 24B, the post-shock wavefront travels in a counter-clockwise, while in FIG. 25B, the rotation is clockwise. The arrows in the figure represent the direction of movement of the wavefronts; the shading of a region represents the phase of the cardiac cycle in the region (e.g., white representing 0 msec of the cycle, and darkest gray representing 110 msec). The wave may approach a region of the heart where only a small percentage of the cells are able to depolarize, preventing effective muscle contraction, but allowing the wave to continue. Indeed, the wave does continue, and by the time it travels completely around the heart, more cells have repolarized, and the wave can continue. The wave will, in fact, continue, and since no blood is being pumped, it is usually a fatal condition unless there is an intervention with a defibrillator. The heart can support multiple such incoherent waves traveling in different directions, so we will apply the term wavelets to these various waves. As the wavelets travel around the heart, the rate at which they complete a 'circuit' is called the VF cycle rate. As the wavelet passes a particular point and depolarizes the cells, the cells will recover, or repolarize before the wavelet returns.

It is desirable to be able to deliver electrical current to specific regions of the myocardium so as to either reduce the extent of the excitable gap region 92 (FIG. 25D) or to terminate pre or post-shock wavelets. The extent of the excitable gap region 92 can be reduced or abolished by delivering current sufficient to depolarize the region of the myocardium that would have been in the excitable gap prior to the defibrillation shock. Using the methods of EIT just described, the resistivity distribution is calculated. Then, using a biodomain model, e.g., as described in IEEE Trans Biomed Eng 46: 260-270, 1999 (Entcheva), a predicted response of the myocardium to an electrical stimulation by the device can be calculated. The bidomain model may be a system of two reaction-diffusion equations, one for the intracellular and the other for the extracellular space linked by transmembrane current. The model simplifies the complex, non-linear behavior of the sarcolemmal ion channels, assuming a passive membrane behavior modeled as a parallel combination of a resistor and a capacitor in order to minimize computational complexity. The model is a system of two differential equations with a constant resistance membrane, Rm:

$$\tilde{N} \times (gi \tilde{N} \Phi i) = \beta (Vm/Rm),$$

$$\tilde{N} \times (ge \tilde{N} \Phi e) = \beta (Vm/Rm),$$

where Vm and Rm are the transmembrane voltage and membrane resistance, respectively, and gi and ge are the intracellular and extracellular conductivity tensors modeling the fiber architecture of the myocardium and β is the cell surface to volume ratio. The excitable gap region 92 is located based on the bidomain calculations, and is shown in FIG. 25D as a hatched region.

Figure 25D:
FIG. 25D is the same as FIG. 25A but with the excitable gap region shown as a cross-hatched area.

Using the previously described EIT methods, the heart is stimulated by one or more pulses in succession before the defibrillation shock by current that is focused in the region of the myocardium that the bidomain model predicted as occupying the excitable gap (hatched region in FIG. 25D). Delivering the pre-shock current to those regions not adequately affected by the defibrillation shock will result in less total energy being required for the combined energies of the pre-defibrillation stimulation and defibrillation shock. A tessellated electrode pattern may be used, e.g., incorporating 16 electrodes for the anterior and posterior electrode pad assemblies.

Figure 25E:
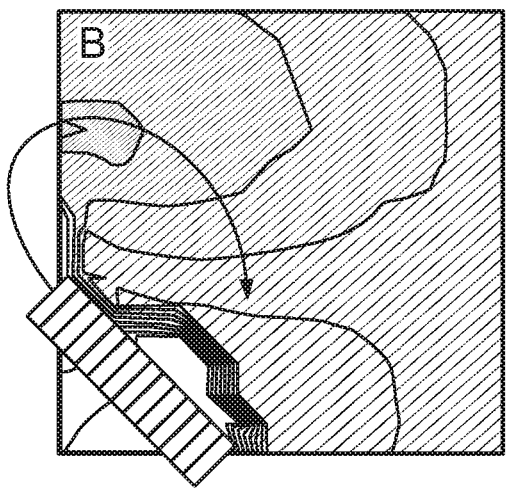
FIG. 25E is the same as FIG. 25B but with a cross hatched area representing the area of an applied quenching stimulus.

In another implementation, an electrode configuration is provided whereby at least some portion of the stimulating electrodes are also connected to filtering and amplification of individual electrocardiographic (ECG) monitoring channels. In a preferred implementation, at least 16 ECG channels are available in the device with the input multiplexed between one electrode on the anterior pad and one electrode on the posterior pad. A sample rate for ECG analysis is preferably 250 Hz, therefore the A/D is sampled at 500 Hz with alternating samples from the anterior and posterior electrode. Employing EIT and solving the forward problem as discussed previously, the distribution of activation wavefronts on the epicardium can be calculated. The path of the activation wavefront can also can calculated, for instance in FIGS. 24B and 25B where the arrows show the path of the activation wavefronts. Using the previously described EIT methods, the heart is stimulated by one or more pulses in succession following the defibrillation shock by current that is focused in the region of the myocardium that lies in the path of the activation wavefront (e.g., the hatched region in FIG. 25E). Depolarizing tissue in front of the activation wavefront will quench the arrhythmogenic activation wavefront when it reaches the refractory, recently stimulated region.

Referring to FIG. 1, variable resistors 71, 72 are replaced by high voltage transistor switches and provided for each of the 16 electrodes. Eight of the 16 anterior electrodes are connected to one H-bridge 10, and the remaining eight are connected to the other H-bridge 11. Alternatively, all 16 may be connected to one H-bridge. By switching the transistor switches 71, 72 at a rate significantly higher than the H-bridge, preferably >50 times faster, the switching of each high voltage transistor 71, 72 can be pulse-width modulated to produce an average current for each electrode. As long as the switching duration is less than approximately 200 microseconds, the myocardium will respond to the average of the pulse-width modulated (PWM) currents. As a result, it is possible also to switch the H-bridge with a period of 120 microseconds, with positive and negative phases of the bridge with a duration of 55 microseconds and a 10 microsecond interphase delay. Each individual high voltage transistor is pulse-width modulated with pulse durations of 5-10 microseconds during both the positive and negative phases of the bridge so as to be able to produce a potentially bipolar voltage at any of the electrodes necessary for a fully functional EIT system.

One possible theory to explain the improvement that some implementations of the invention may achieve in defibrillation efficacy (understanding, of course, that the invention is not limited to this theory) is as follows: As stated previously, the theory of Virtual Electrode Polarization (VEP) describes the phenomena by which, because of current flow within a partially conductive medium (the myocardium) contained within another partially conductive medium (blood of the cardiac chambers, lungs, interstitial fluids and other organs within the thoracic cavity), myocardial polarization during defibrillation is characterized by the simultaneous presence of positive and negative areas of polarization adjacent to each other. "Phase Singularity" as defined within the context of VEP is a critical point that is surrounded by positively polarized (equivalent to "depolarized" in the conventional electrophysiology nomenclature), non-polarized and negatively polarized (equivalent to "hyperpolarized") areas. These phase singularities are the source of re-initiation of fibrillation. Post shock excitations initiate in the non-polarized regions between the positively and negatively polarized areas through a process termed "break excitation." The break excitations propagate through the shock-induced non-polarized regions termed "excitable gaps", and if the positively polarized regions have recovered excitability, then a re-entrant circuit at which fibrillation may initiate is formed. With biphasic defibrillation, the second phase of the shock nullifies the VEP effect by depolarizing the negatively polarized tissue. Since less energy is needed to depolarize repolarized tissue than further depolarize already depolarized tissue, effective biphasic defibrillation achieves nearly complete depolarization of the myocardium by reversing the negative polarization while maintaining the positive polarization. There remain, however, excitable gaps even with biphasic and multiphasic waveforms, albeit reduced in scope relative to monophasic waveforms, and there still remains the potential for significant improvement of the efficacy of biphasic defibrillation waveforms.

Figure 13:
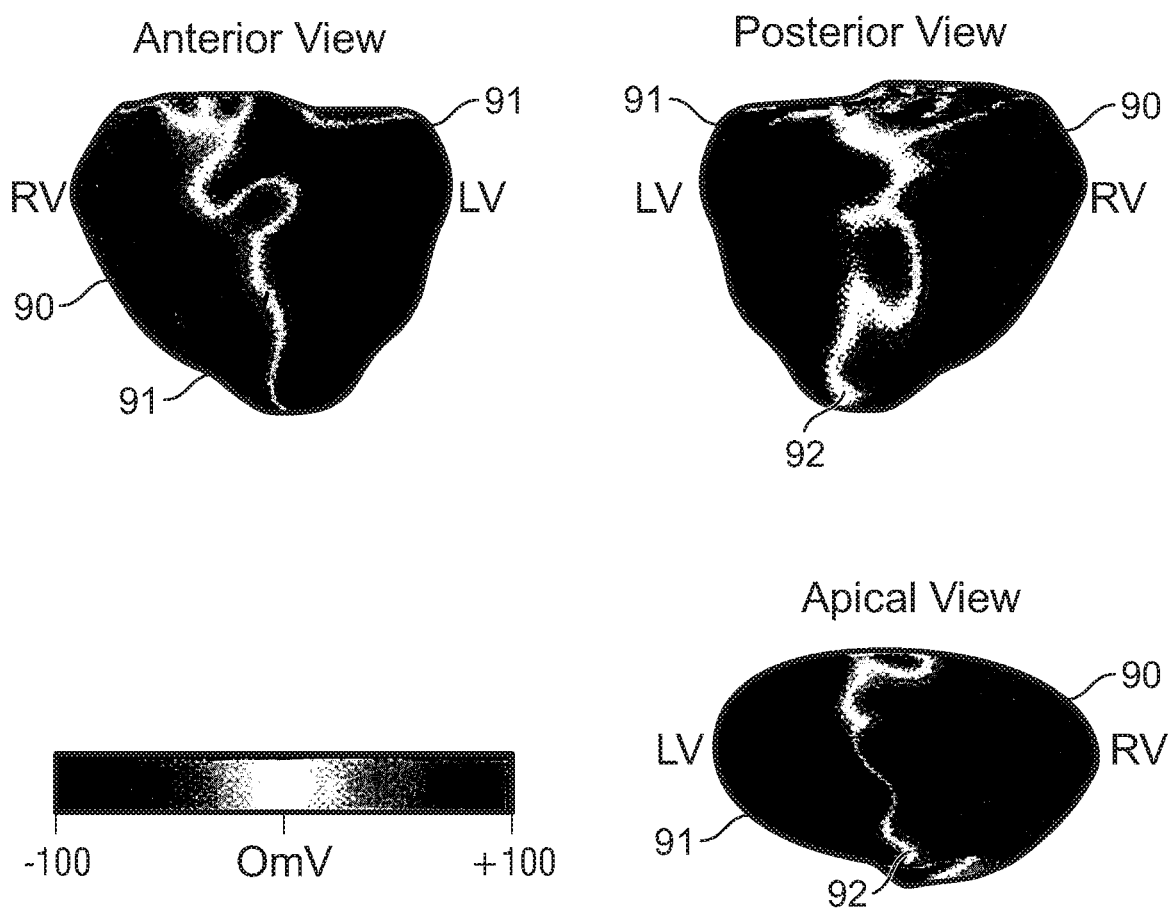
FIG. 13 shows a simulation of the effects on the heart due to a monophasic defibrillation pulse as modeled using the Virtual Electrode Theory.
Figure 14A:
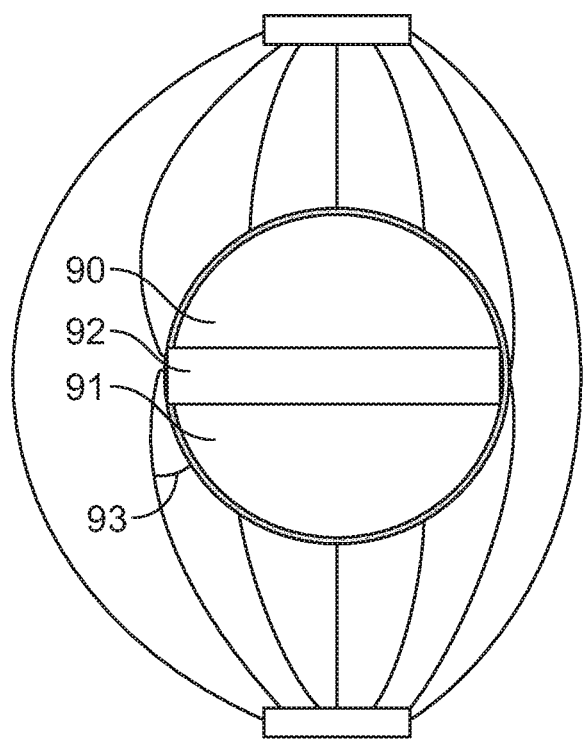
FIG. 14a, 14b depict, diagrammatically, what occurs when the area of the electrodes is varied.
Figure 14B:
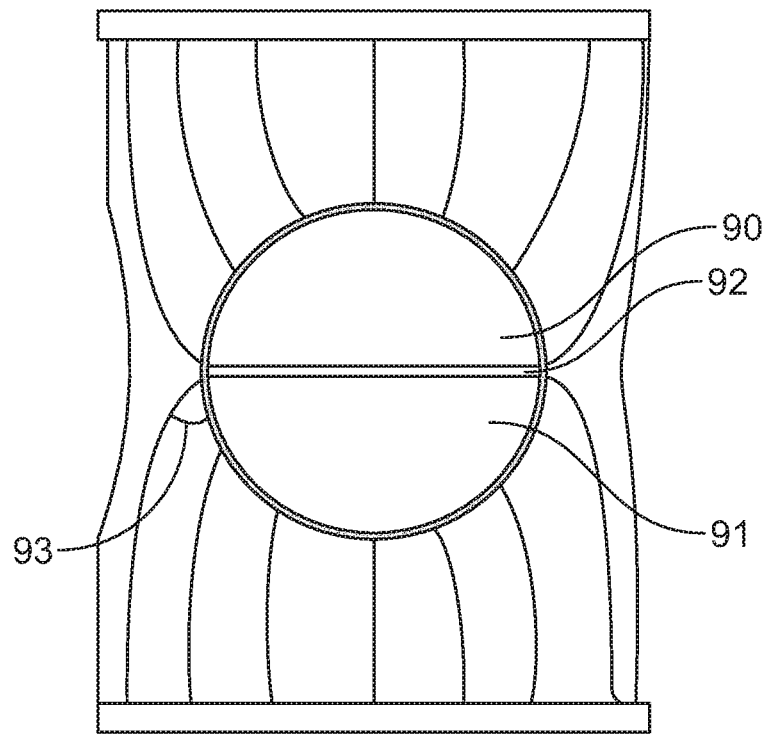

FIG. 13 shows the results of a simulation in a study by Efimov (Am J Physiol Heart Circ Physiol 2000; 279:H1055-70). The lighter grey region 90 is a region of positive polarization and the black region 91 is one of negative polarization. The white region 92 is the excitable gap region. FIGS. 14a and 14b depict, in schematic view, what occurs when the area of the electrodes is varied. As can be seen, by increasing the size of the electrodes, the contact angle, φ 93, of the electric field lines is increased in the region of the excitable gap, thereby reducing the areal extent of the excitable gap. Reduction of the areal extent of the excitable gap, improves the chances for a successful defibrillation and reduces defibrillation thresholds.

In other implementations, the waveforms may each be composed of a sequence of pulses. The relative timing of the current vectors may be designed so that the pulse sequences are interposed with non-overlapping individual pulses.

Figure 26:
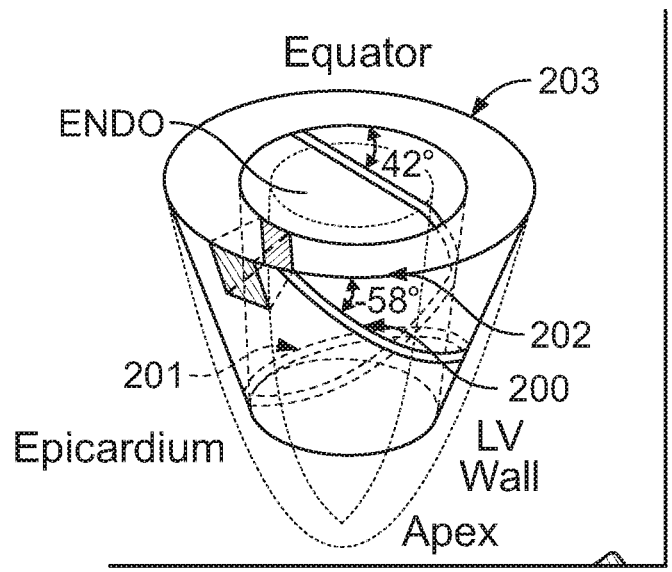
FIG. 26 provides a simplified, perspective view of the ventricles, showing the generally spiral orientation of the muscle fibers.
Figure 27:
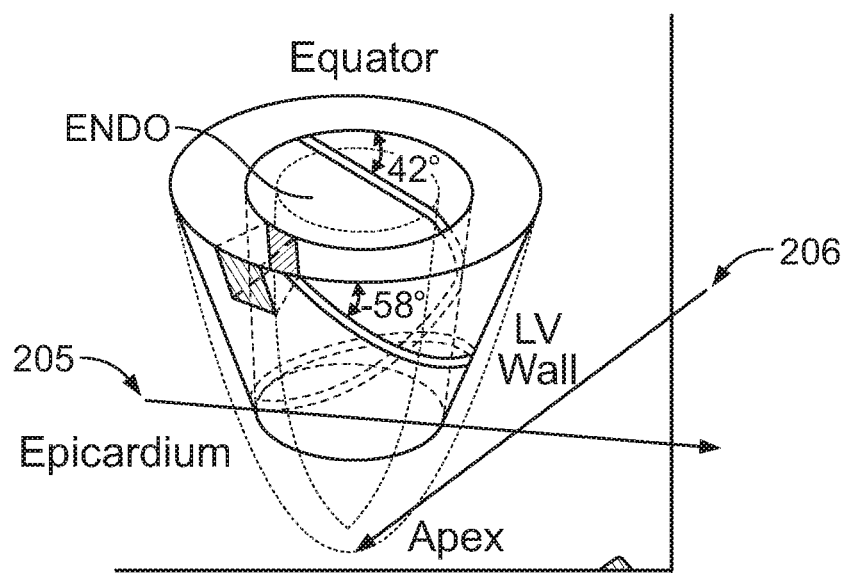
FIG. 27 provides a simplified, perspective view of the ventricles, showing two possible current vectors (for a two-vector approach) generally aligned with the muscle fibers.

Referring to FIGS. 26 and 27, in another implementation the electrode pairs may be configured so that, at the heart, the electrical current vector 205 for one pair is substantially aligned with (e.g., parallel to the long axis of) the myocardial fiber orientation of the epicardium 200 on the anterior portion 202 of the heart, while the current vector 206 for the other pair of electrodes is substantially aligned with the fiber orientation of the epicardium 201 on the posterior portion 203 of the heart. In a three-dimensional conductive medium, the current distribution is also three-dimensional, with each point within the volume best described as a 3-space vectorial value specifying the current density. Thus, the term "current vector" is a simplification of this more general concept, and describes a volume-averaging of the current density that has been normalized to provide a vector that describes the average direction of current flow within a volume. Myocardium has been shown to have anisotropic conductivity, with the long axis along the fiber orientation having the higher conductivity. This method thus enhances current flow within the myocardium (as it lowers the impedance along paths through the myocardium, causing more current to flow through the myocardium). This method is also applicable to implementations containing more than two pairs of electrodes. For instance, four pairs of electrodes may be used with the electrical current vector for each aligned with the fiber orientation of a portion of the heart. In one implementation, the four portions of the heart are the left anterior, right anterior, right posterior, and left posterior.

Figure 28A:
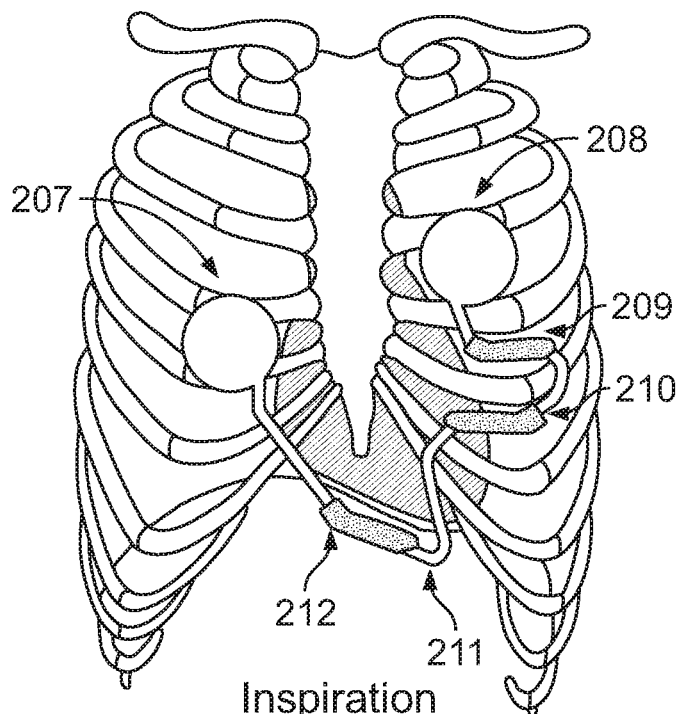
FIGS. 28A and 28B show an implanted defibrillator and electrodes that provide another implementation of the two vector approach in which the vectors are aligned with muscle fibers.
Figure 28B:
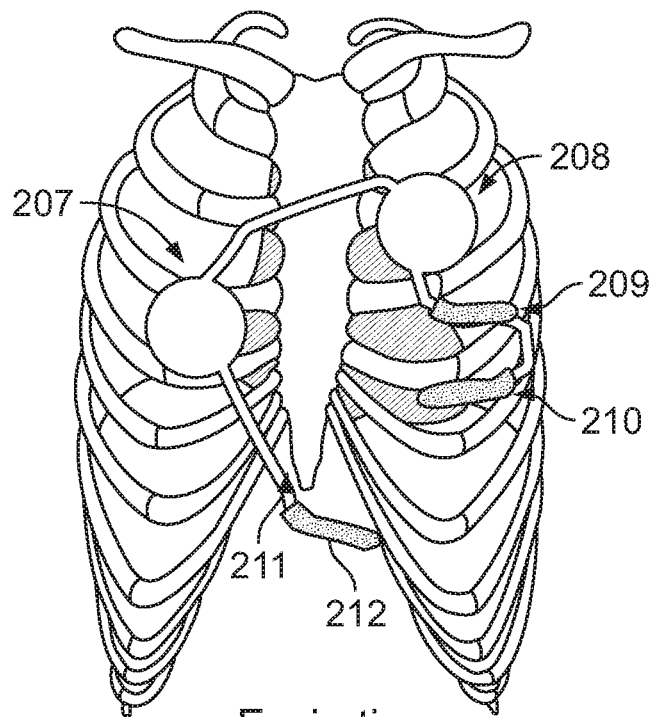

Referring to FIGS. 28A and 28B, the method described in the previous paragraph may also be applied to provide a "leadless" implanted defibrillator system wherein all the stimulating electrodes and the device housing of the implanted cardiac stimulation device is external to the thoracic cage but implanted subcutaneously. Commonly termed implanted cardioverter-defibrillators (ICDs), the devices have required for at least one of the stimulating electrodes to be placed on a catheter placed within the heart, typically in the right ventricle and superior vena cava in order to reduce the energy required to defibrillate, thus minimizing the size of the implanted device.

Referring to FIG. 28A, two separate defibrillator housings 207, 208 are provided along with stimulating electrodes 209, 210, 212. The corresponding stimulating electrodes 209, 210 for the right atrial housing 207, and the corresponding stimulating electrode 212 for left atrial housing 208, result in current vectors 205, 206 substantially aligned with the fiber orientation of the myocardinum in the posterior and anterior portions of the heart, respectively. The right atrial stimulating electrodes 209, 210 (which electrically serve as one electrode) are positioned over the intercostal spaces to reduce defibrillation impedance and are mounted onto the adjacent ribs with mounting hardware of a suitable material such as stainless steel alloys (e.g., 316L), cobalt-alloy F90, or titanium, or sutured into place. Using two pairs of stimulating electrodes provides a more uniform current distribution across a larger region of the heart. Because of the human heart's angular orientation to the rib cage, the intercostal spaces are oriented perpendicular to the perimeter of the heart in projection. Thus, aligning a single stimulating electrode with the intercostal space may reduce the impedance and increase therapeutic current levels, but as a result myocardial current distribution becomes more non-uniform. This current density intensification is eliminated by placing at least two commonly connected stimulating electrodes 209, 210 in different intercostal spaces. The particular intercostal spaces may be adjacent or may have intervening, non-stimulating intercostal spaces.

Figure 29:
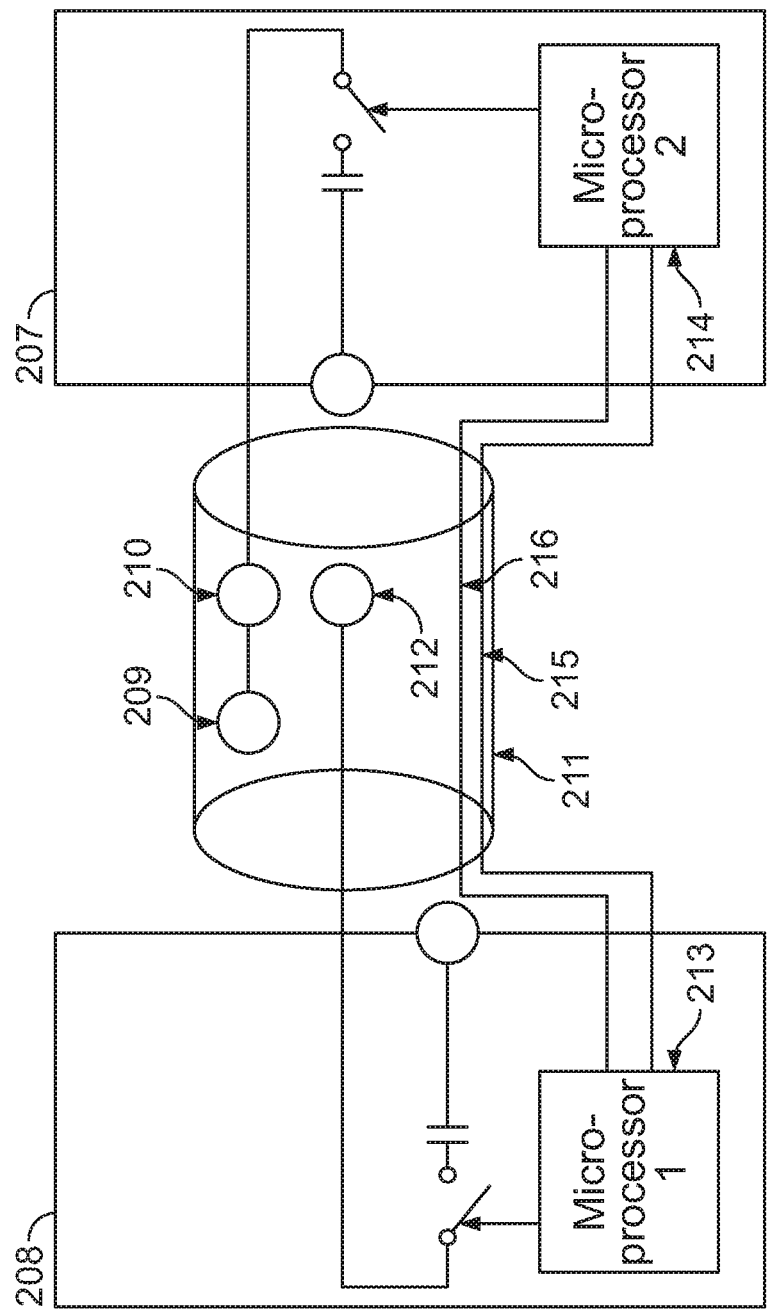
FIG. 29 shows an electrical schematic of the implementation of FIG. 28B.

Referring to FIG. 29, the housings 207, 208, which are configured as "active" cans with all or some portion of the housing providing stimulation to the stimulating electrodes, are connected to conductors contained in a common sheath 211 composed of a biocompatible material such as a silicone-polyurethane copolymer. The stimulating electrode 212 corresponding to the left atrial housing 208 is located just below the xyphoid process. Preferably, this electrode is oriented parallel to the perimeter of the projection of the heart onto the rib cage to provide better current distribution. Microprocessors 213, 214 communicate via conductors 215, 216 to provide status information and synchronization of defibrillation pulses during defibrillation. Preferably, one of the microprocessors functions as a primary processor. The primary processor is responsible for functions such as self tests and communication with devices outside the body that are better performed in a centralized rather than distributed manner, ECG signal processing may also be localized to the primary processor, and the secondary processor may perform the single function of providing a defibrillation pulse at a time deemed appropriate by the primary processor, which communicates that time via conductors 215, 216. Preferably, one wire 215 is a single-wire serial interface providing a variety of status and data between the processors, while the second wire 216 is a hardware-level interrupt to provide microsecond-level control of the timing of the secondary defibrillation pulse. In a related implementation shown in FIG. 28B, conductors for electrodes 209, 210 that are part of the defibrillation circuit contained in housing 207 pass through left atrial housing 208, and the conductor 212 passes through housing 207, in order to provide an alternative configuration with a minimal number of wires within the patient.

In another implementation, an imaging method such as ultrasound or magneto-resonant imaging (MRI) may be used to determined the exact location and angular orientation of the heart within the thoracic cavity prior to implantation of the device so as to obtain improved positioning to produce current vectors 205, 206 in better alignment with the fiber orientation of the epicardium. The defibrillator housings 207, 208 and stimulating electrodes 209, 210, 212 are positioned so as to provide closer alignment of the expected current vectors 205, 206 to the fiber orientations 200, 201. In the implementation where MRI is used, external transthoracic pacing electrodes may be applied to the patient in the positions such as is shown in FIG. 8a or 8b prior to the process of obtaining the MRI. A test pacing pulse or pulses may then be delivered to the patient that is synchronized with the MRI excitation pulses so as to produce a three dimensional representation of the current vector space that will show the myocardial fiber orientation for use in determining the positioning of the housings 207, 208 and stimulating electrodes 209,210, 212.

Figure 15:
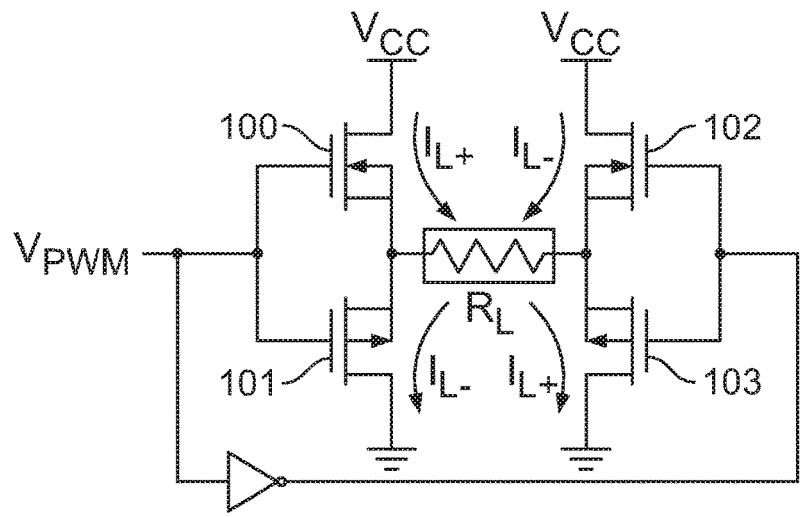
FIG. 15 is an electrical schematic of an H-Bridge Class D configuration circuit.
Figure 16:
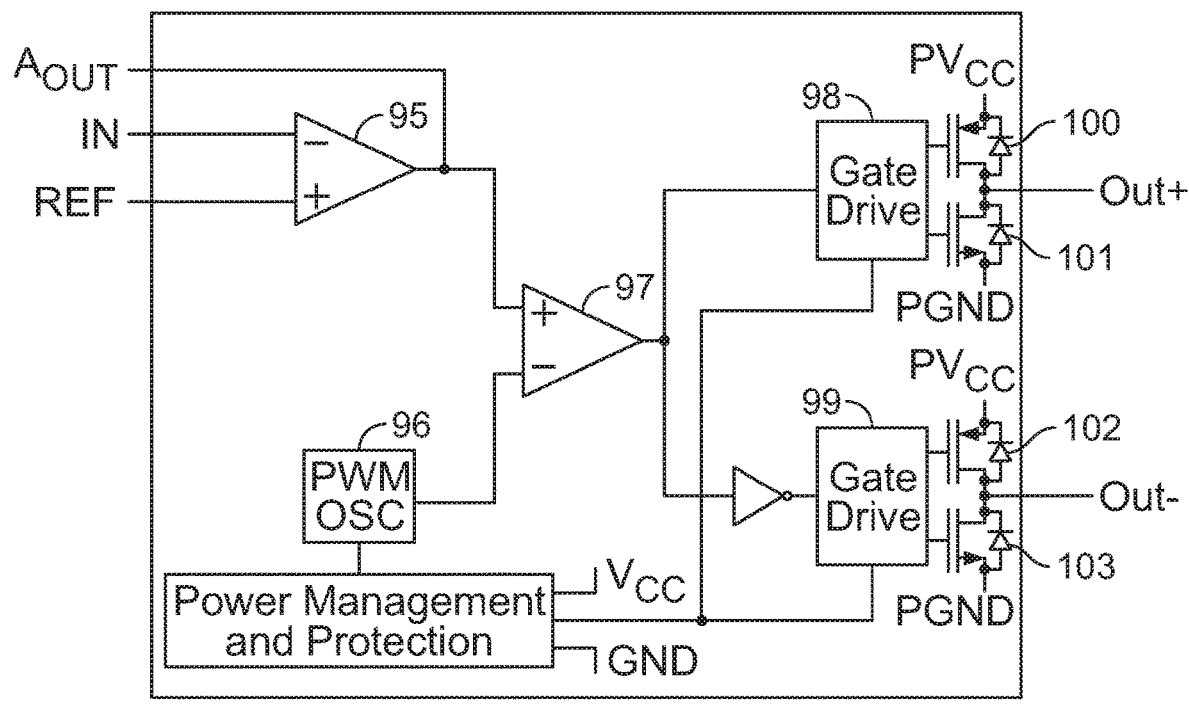
FIG. 16 is an electrical schematic of circuitry driving an H-bridge Class D configuration circuit.
Figure 17:
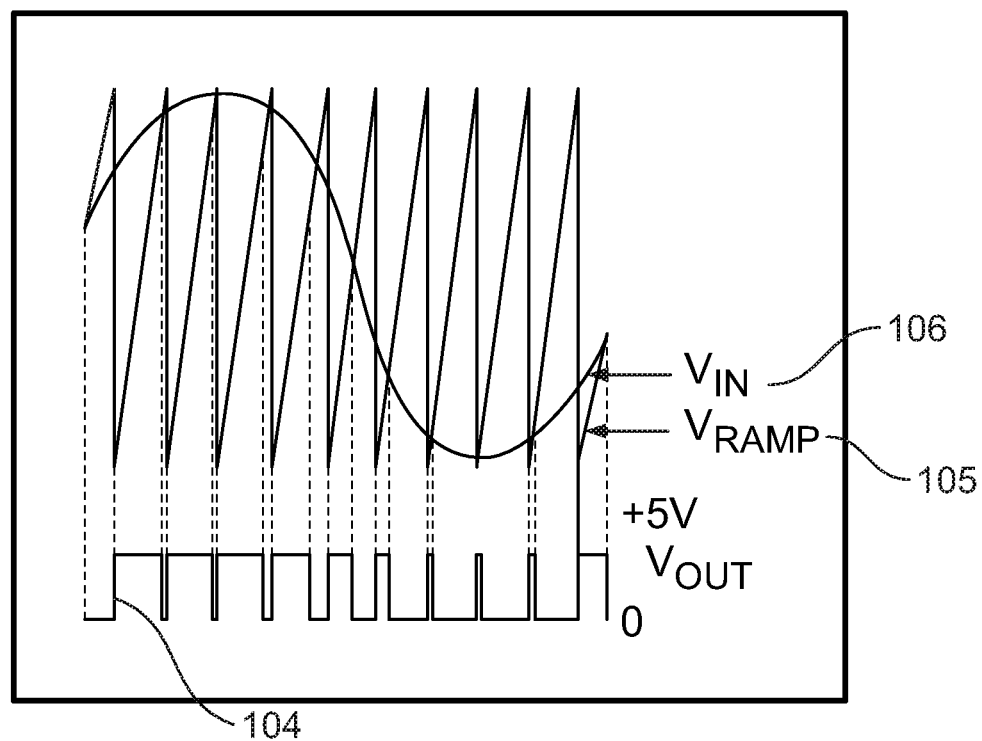
FIG. 17 are waveforms produced by the H-bridge Class D configuration circuit.

In another implementation, resistance circuits 55, 56 are eliminated and the waveform shape, and thus also the first phase average current, is adjusted by pulse width modulating the switches in the H-bridges 10, 11. This configuration is the Class D amplifier configuration, known to those skilled in the art of amplifier design. In its simplest form, a switch-mode amplifier consists of an H-bridge and a load as shown in FIG. 15. Amplifiers are typically classified by their output stages. Of the common output-stage topologies (Classes A, B, AB, and D), Class D amplifiers exhibit the highest efficiency. A linear output stage (Class A, B, or AB) draws considerable bias current while sourcing and sinking current into a speaker making them not particularly well suited to high voltage designs. A nonlinear (Class D) output stage eliminates this bias current. In the preferred implementation, as shown in FIG. 16, the Class D amplifier consists of an input preamplifier 95 for isolating, filtering and level shifting the control voltage from the processing means 5, a sawtooth oscillator 96, a comparator 97, two MOSFET drivers 98, 99, and the H-bridge switches 100-103. The comparator samples the input signal, with the oscillator frequency determining the duration of the sampling period. Thus, the oscillator frequency is an important factor in the overall performance of a Class D amplifier. As shown in FIG. 17, the comparator output 104 is a pulse-width modulated (PWM) square wave that drives the H-bridge. The PWM square wave 104 is created by a comparator whose inputs are the sawtooth ($V_{RAMP}$) 105 and the control signal ($V_{IN}$) 106. The H-bridge then outputs the square wave differentially. For a given input level, the comparator output is a duty-cycle modulated square wave with period determined by the sawtooth frequency. The PWM square wave controls the H-bridge drivers 100-103, turning opposite pairs of MOSFETs off and on, thereby reversing current to the load within a single period. The output may be filtered by capacitor filters or inductor/capacitor filter combinations which remove high-frequency content from the H-bridge square wave output.

Figure 18:
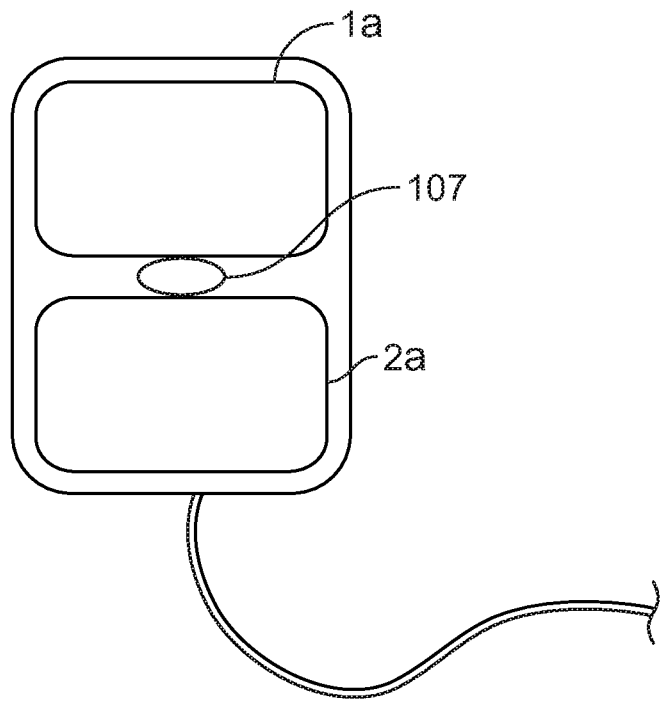
FIG. 18 is a plan view of an integrated defibrillation pad including an ultrasonic gel window for application of an ultrasonic probe.

Alternatively, the measurement of the thoracic cavity may be carried out using an ultrasound transducer capable of imaging the heart and surrounding tissue. An ultrasound transducer may be incorporated into an integrated defibrillation pad, as shown in FIG. 18. In a preferred implementation, an opening in the center of the electrode is provided that is covered over with an ultrasonic-conducting gel 107. The gel is a bilayer structure with a more aggressive adhesive provided on the face opposite to the patient for attaching the ultrasonic probe prior to use.

Figure 19:
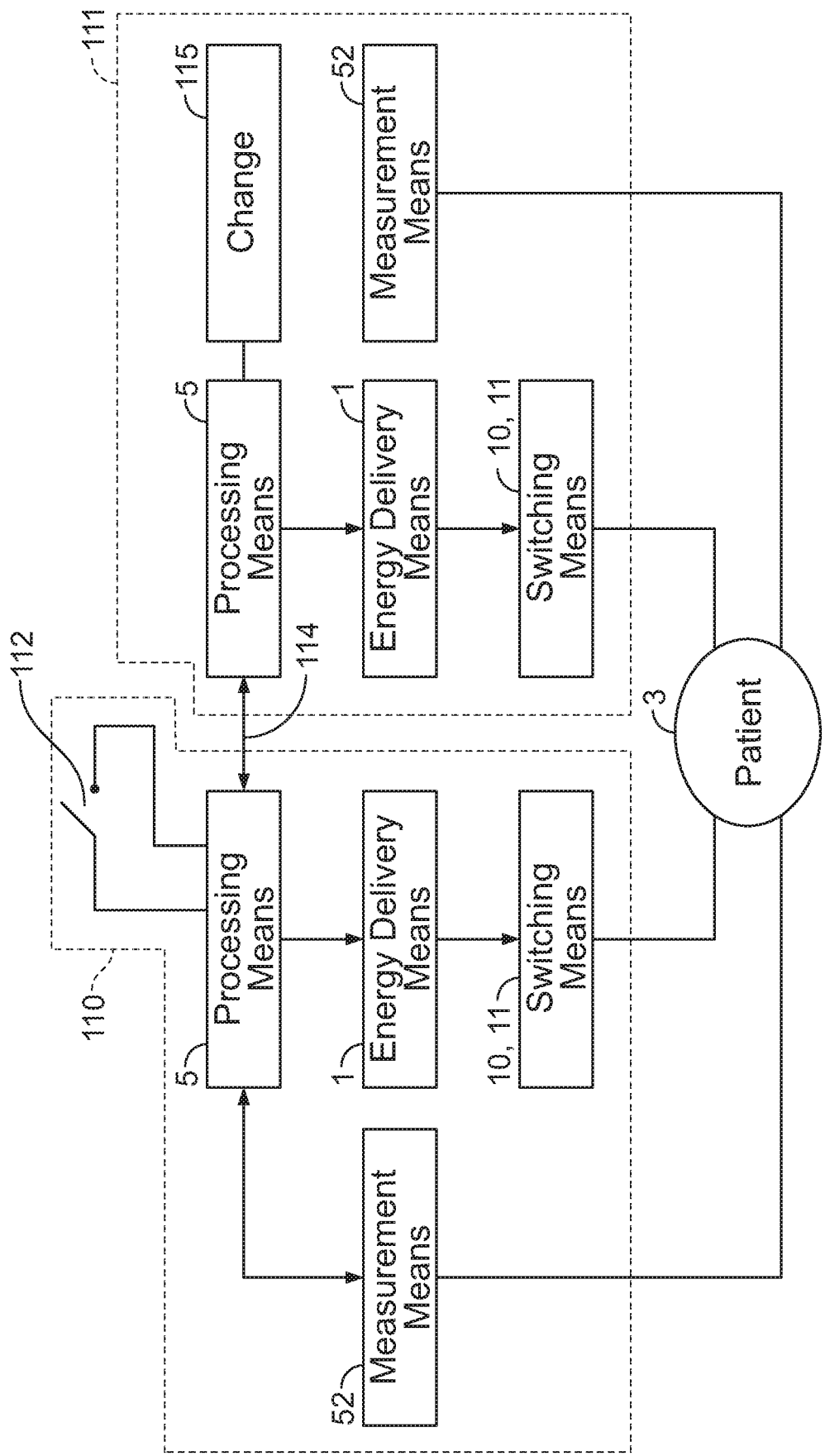
FIG. 19 is a block diagram of an implementation with dual defibrillators.

In other implementations, there may be two or more separate defibrillators, as shown in FIG. 19. The first defibrillator 110 acts as the master defibrillator, while additional defibrillators 111 function as slave defibrillators whose energy is delivered synchronously with that of the master defibrillator 110. Synchronization is provided by communication means 114. Preferably, the communication means 114 is implemented as a simple switch. In a conventional defibrillator, the delivery of energy is initiated via the closure of a discharge switch 112 located on the front panel or on a set of defibrillation paddles. The closure of the switch initiates the defibrillation sequence under the control of processing means 5. Charging of the high voltage capacitors on both defibrillators 110, 111 is initiated via the charge-control user inputs 115. At the appropriate time, the clinician will press the discharge button 112. This causes the processing means 5 on the first defibrillator 110 to close a slave discharge switch that initiates the discharge sequence on the second defibrillator 111, at which time the first defibrillator 110 also initiates its discharge sequence. The wiring for the communication means 114 is preferably configured such that the wires are located within the same cable as the energy delivery wires, thus reducing any additional cabling. The communication means 114 may also incorporate digital communication methods which provide additional information about defibrillator status.

Figure 20:
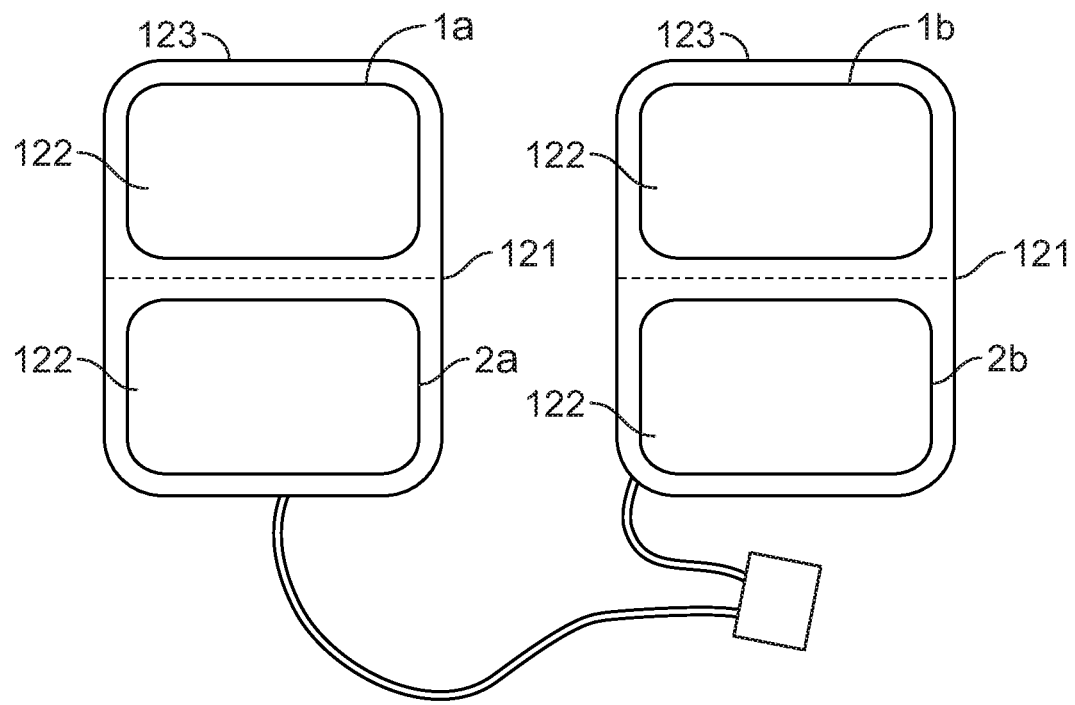
FIG. 20 is a plan view of two integrated defibrillation electrode pads, electrically connected with a common connector in a dual defibrillator system.

The defibrillator pad 123 may integrate all connections into a single connector 120 as shown in FIG. 20. The defibrillator pads may be constructed such that a seam line 121 is located between the active areas 122 of the pad 123 where the seam line 121 is of higher compliance than the active areas such that the pad 123 can be folded during storage without creasing the active areas.

Figure 22:
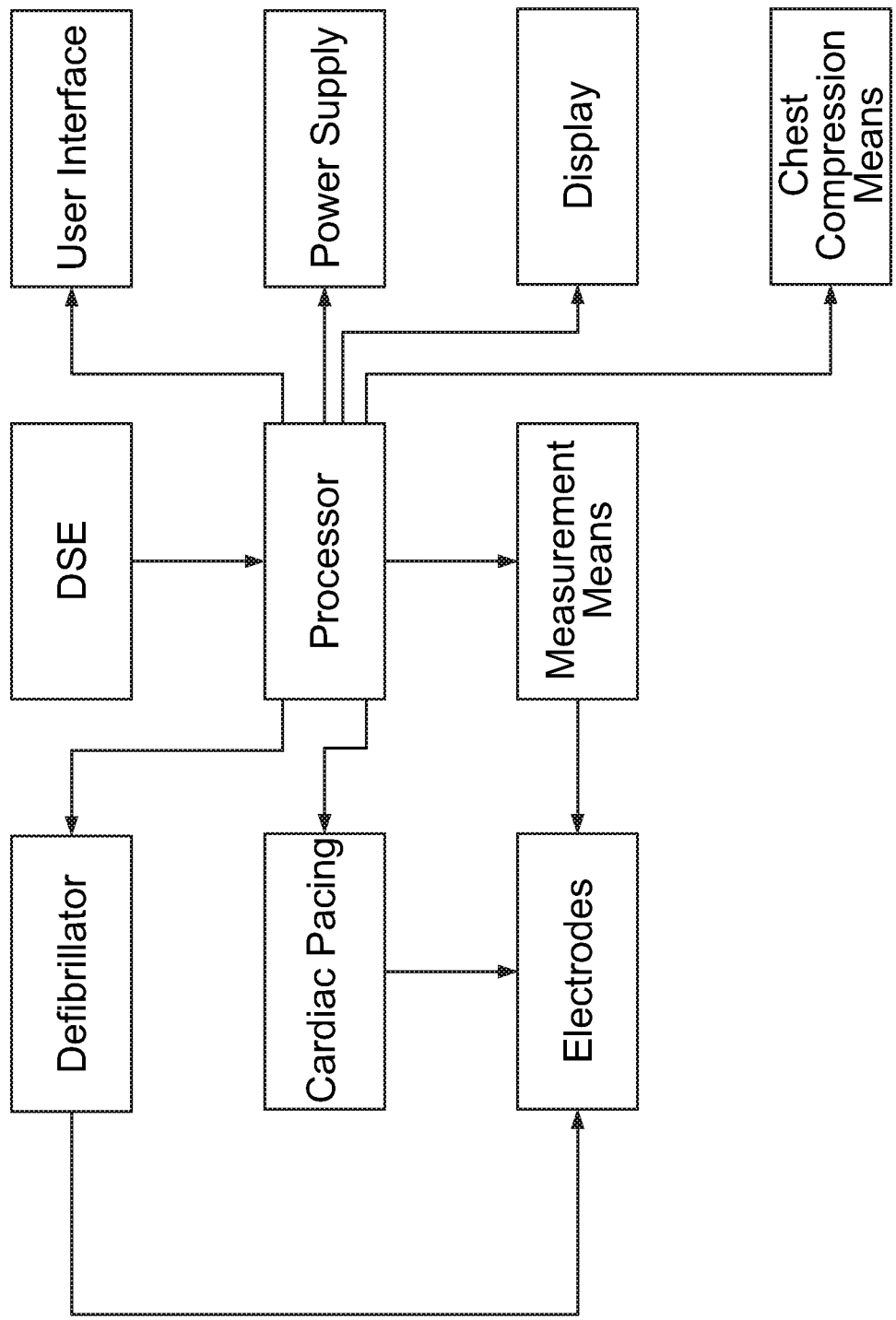
FIG. 22 is a block diagram of an integrated resuscitation system implementation.
Figure 23:
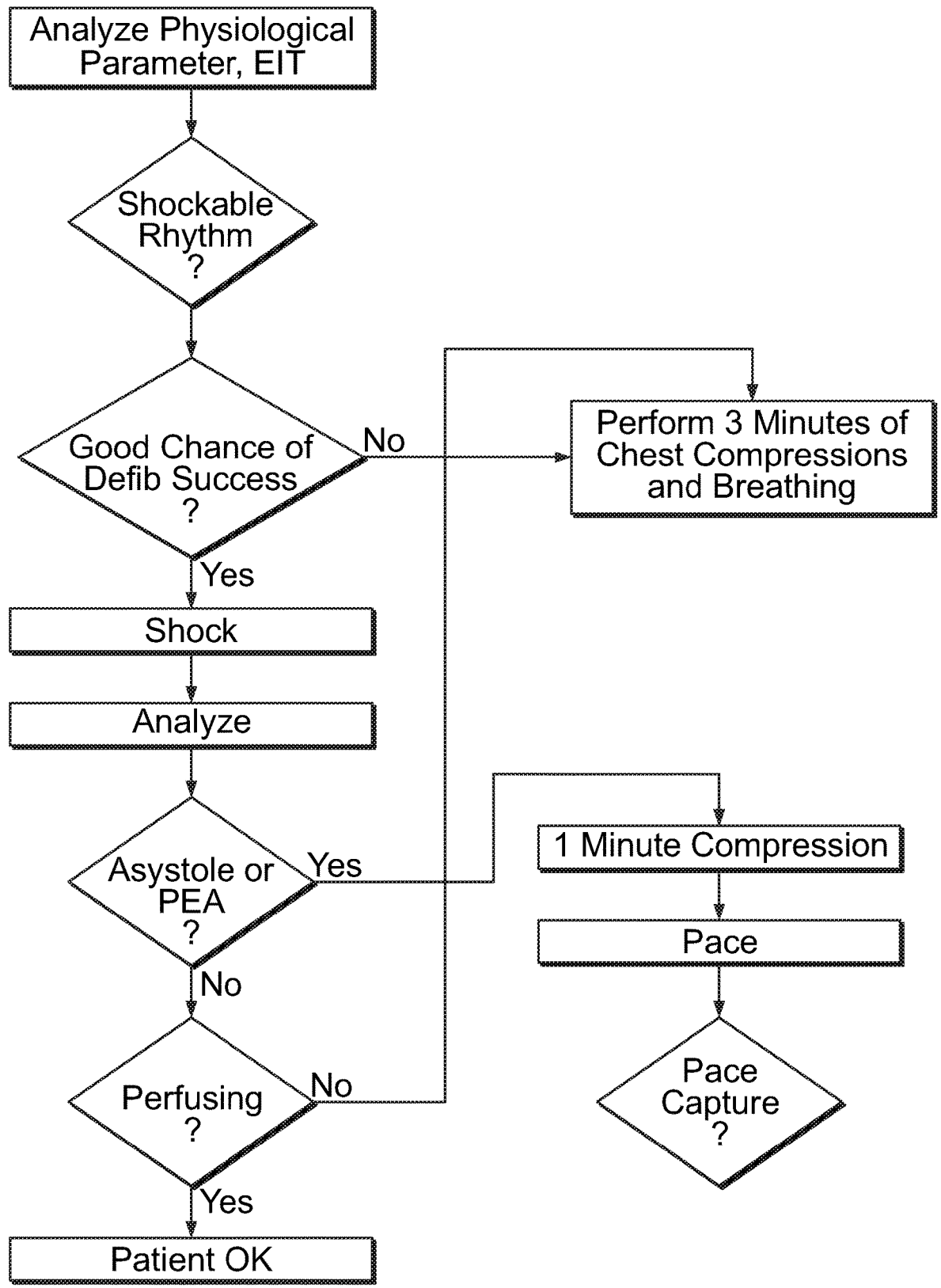
FIG. 23 is a decision flowchart for the integrated resuscitation system.

In another implementation, a physiological parameter, e.g., the electrocardiograph (ECG), is measured in conjunction with the EIT image, and an estimate is made by the device of the chances for a successful defibrillation shock based analysis of ECG data. Depending on the estimate of shock success, decisions as to the proper treatment to provide the patient are made in a coordinated resuscitation effort that includes both defibrillation and chest compressions, which can be provided manually in response to prompts, or in a semi-automated or fully automated fashion. The block diagram and flow chart for such a system is shown in FIGS. 22 and 23.

One or more additional electrodes 125 may be provided for diaphragmatic stimulation (DS) and may be incorporated into the anterior electrode such that the DS Electrode (DSE) is located over the patient's diaphragm as shown in FIG. 21. Diaphragmatic stimulation induces air exchange in the lungs during cardiopulmonary resuscitation (CPR) for improved oxygenation. The return path for the stimulation current from the DSE is through one of the pre-existing electrodes. Utilizing EIT or other imaging methods, the current distribution may be adjusted to achieve optimal stimulation, as described previously in this patent. The DSE may be integrated with defibrillation and cardiac pacing to provide a coordinated resuscitation effort in an automated or semi-automated fashion. The integrated resuscitation may also incorporate a means of providing chest compressions, such as a piston-based system manufactured by Michigan Instruments (Michigan) or a constricting band system manufactured by Revivant Corp. (California). FIG. 23 shows a decision flow chart of one possible integrated resuscitation protocol.

Many other implementations of the invention other than those described above are within the invention, which is defined by the following claims. The invention applies to both defibrillation and cardioversion; in the claims, references to defibrillation should be interpreted as also encompassing cardioversion. Some implementations of the invention are broader than defibrillation and cardioversion.

What is claimed is:

1. A defibrillation system for synchronized cardioversion of a patient comprising:
  a first housing comprising:
    a first shock delivery circuit configured to be controlled by a first processor for delivery of a first shock;
    a measurement circuit configured to receive electrocardiogram (ECG) signals and measure ECG parameters based on the ECG signals, and
    the first processor configured to:
      analyze the ECG parameters, and
      initiate communication of a synchronization signal for a second processor for delivery of a second shock; and
  a second housing that is separate from and external to the first housing, the second housing comprising:
  a second shock delivery circuit, and
  the second processor, wherein the second processor is configured to:
    receive the communication of the synchronization signal from the first processor, and
    control the second shock delivery circuit to deliver the second shock in response to the synchronization signal.

2. The defibrillation system of claim 1 wherein the delivery of the second shock is based on the ECG parameters.

3. The defibrillation system of claim 1 comprising:
  three or more electrodes configured to attach to the patient and provide two or more discharge pathways; and
  at least one measurement circuit configured to:
    couple to the three or more electrodes, and
    measure one or more electrical parameters of the patient,
  wherein at least one of the first processor and the second processor is configured to:
    based on the one or more measured electrical parameters, determine internal impedances, for the patient, corresponding to the two or more discharge pathways, and
    control at least one parameter of at least one of the first shock and the second shock based on the determined internal impedances.

4. The defibrillation system of claim 3 wherein the one or more electrical parameters comprise a current that passes through the patient.

5. The defibrillation system of claim 3 wherein the one or more electrical parameters comprise an induced voltage at a plurality of locations on the patient.

6. The defibrillation system of claim 3 wherein the at least one of the first processor and the second processor is configured to independently control the at least one parameter for each of the first shock and the second shock based on the internal impedances.

7. The defibrillation system of claim 3 wherein the at least one parameter comprises at least one of amplitude, tilt, duration first phase duration, second phase duration, current, voltage, and first phase average current.

8. The defibrillation system of claim 3 wherein at least the first processor is configured to use electrical impedance tomography (EIT) and determine the internal impedances as an internal impedance distribution.

9. The defibrillation system of claim 8 wherein one or more of the first processor and the second processor is configured to determine a predicted response of the myocardium of the patient to at least one of the first shock and the second shock based on a model and the internal impedance distribution.

10. The defibrillation system of claim 9 wherein the model comprises a biodomain model.

11. The defibrillation system of claim 9 wherein the predicted response comprises an indication of one or more excitable gap regions of the myocardium of the patient.

12. The defibrillation system of claim 11 wherein at least the second processor is configured to control at least one of the first shock delivery circuit and the second shock delivery circuit to deliver one or more electrical pulses in succession prior to at least one of the first shock and the second shock wherein a current density from the one or more electrical pulses is configured to be directed towards the one or more excitable gap regions of the myocardium of the patient via a predetermined physical arrangement of the three or more electrodes.

13. The defibrillation system of claim 3 wherein the measurement circuit comprises individual ECG monitoring channels and further wherein at least a portion of the three or more electrodes are coupled to the individual ECG monitoring channels.

14. The defibrillation system of claim 13 wherein one or more of the first processor and the second processor is configured to determine an epicardial activation wavefront distribution.

15. The defibrillation system of claim 13 wherein one or more of the first processor and the second processor is configured to determine an epicardial activation wavefront path.

16. The defibrillation system of claim 13 comprising at least sixteen ECG monitoring channels and at least sixteen electrodes.

17. The defibrillation system of claim 16 wherein the first processor is configured to sample ECG signals at a sample rate of approximately 250 Hz.

18. The defibrillation system of claim 13 wherein the three or more electrodes are distributed between at least one anterior electrode pad assembly and at least one posterior electrode pad assembly and further wherein the one or more of the first processor and the second processor is configured to sample the ECG signals with alternating samples from the at least one anterior electrode pad assembly and the at least one posterior electrode pad assembly.

* * * * *

UNITED STATES PATENT AND TRADEMARK OFFICE
CERTIFICATE OF CORRECTION

PATENT NO. : 11,097,118 B2  
APPLICATION NO. : 15/879532  
DATED : August 24, 2021  
INVENTOR(S) : Gary A. Freeman et al.

It is certified that error appears in the above-identified patent and that said Letters Patent is hereby corrected as shown below:

In the Claims

Column 25, Line 11, Claim 7, delete "duration first phase duration", insert --duration, first phase duration--

Column 25, Line 24, Claim 10, delete "biodomain", insert --bidomain--

Column 26, Line 28, Claim 18, after "wherein", delete "the"

Signed and Sealed this  
Twenty-ninth Day of March, 2022

Drew Hirshfeld  
*Performing the Functions and Duties of the*  
*Under Secretary of Commerce for Intellectual Property and*  
*Director of the United States Patent and Trademark Office*